United States Patent
Fiechtner et al.

(10) Patent No.: US 10,520,498 B2
(45) Date of Patent: Dec. 31, 2019

(54) DEVICES AND TECHNIQUES FOR ORAL FLUID COLLECTION AND SEROPROTECTION TESTING

(71) Applicant: Becton, Dickinson and Company, Franklin Lakes, NJ (US)

(72) Inventors: Michael D. Fiechtner, Poway, CA (US); Francis R. Go, San Diego, CA (US); Myron Levine, Columbia, MD (US); Scott Castanon, Carlsbad, CA (US)

(73) Assignees: Becton, Dickinson and Company, Franklin Lakes, NJ (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/919,632

(22) Filed: Mar. 13, 2018

(65) Prior Publication Data

US 2018/0267030 A1    Sep. 20, 2018

Related U.S. Application Data

(60) Provisional application No. 62/471,237, filed on Mar. 14, 2017.

(51) Int. Cl.
*G01N 1/28* (2006.01)
*G01N 33/543* (2006.01)
(Continued)

(52) U.S. Cl.
CPC ... *G01N 33/54306* (2013.01); *A61B 10/0051* (2013.01); *G01N 1/28* (2013.01); *G01N 33/6854* (2013.01)

(58) Field of Classification Search
CPC ............. G01N 33/54306; G01N 1/28; G01N 33/6854; A61B 10/0051
See application file for complete search history.

(56) References Cited

U.S. PATENT DOCUMENTS 1,853,238 A  4/1932  Shields
5,511,654 A  4/1996  de la Rocha
(Continued)

FOREIGN PATENT DOCUMENTS

WO  WO 1995/025948  9/1995
WO  WO 2011/095599  8/2011

OTHER PUBLICATIONS

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.
(Continued)

*Primary Examiner* — Melanie Brown
(74) *Attorney, Agent, or Firm* — Knobbe Martens Olson & Bear LLP

(57) ABSTRACT

Seroprotection analysis systems, kits, and techniques are described for testing oral fluid for the presence of protective levels of antibodies of interest. In one aspect, the presence of protective levels of target antibodies indicates a test subject has achieved a target seroprotection level, such as but not limited to a target seroprotection level following vaccination. A collection kit can include a swab that enables collection of oral fluid containing antibodies from both dentulous and edentulous individuals, a container that can be pre-filled with an extraction solution, and a nozzle that can be coupled to the container to form a fluid-tight device. A user can use the nozzle to seal the swab in the container and to compress the swab within the container. After or during compression, the solution can be dispensed from the fluid-
(Continued)

tight device, such as by inverting the fluid-tight device to flush the swab with the buffer solution and to transfer the fluid to a detection device through a channel in the nozzle. The detection system can be an assay reader device.

20 Claims, 19 Drawing Sheets

(51) Int. Cl.
*G01N 33/68* (2006.01)
*A61B 10/00* (2006.01)

(56) References Cited

U.S. PATENT DOCUMENTS

| | | | |
|---|---|---|---|
| 5,871,905 A * | 2/1999 | Thieme | G01N 33/54313 |
| | | | 435/5 |
| 7,114,403 B2 | 10/2006 | Wu | |
| 2004/0018634 A1 | 1/2004 | Hajizadeh | |
| 2004/0237674 A1 * | 12/2004 | Wu | A61B 10/0051 |
| | | | 73/864 |
| 2005/0136553 A1 | 6/2005 | Kaylor et al. | |
| 2009/0143699 A1 | 6/2009 | Wu | |
| 2010/0077843 A1 | 4/2010 | Doraisamy et al. | |
| 2010/0288691 A1 * | 11/2010 | Shigesada | B01D 69/10 |
| | | | 210/455 |
| 2011/0239793 A1 * | 10/2011 | Ohtsuka | A61B 10/0038 |
| | | | 73/864.63 |
| 2014/0309556 A1 | 10/2014 | Fletcher et al. | |
| 2015/0132795 A1 | 5/2015 | Griswold et al. | |
| 2015/0219531 A1 * | 8/2015 | Hawkins | B01F 5/0608 |
| | | | 73/863.23 |
| 2016/0041167 A1 | 2/2016 | Campbell et al. | |

OTHER PUBLICATIONS

Becton Dickinson—Veritor™ System—for Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

* cited by examiner

DEVICES AND TECHNIQUES FOR ORAL FLUID COLLECTION AND SEROPROTECTION TESTING

CROSS-REFERENCE TO RELATED APPLICATIONS

The present application claims priority under 35 U.S.C. § 119(e) to U.S. Provisional Patent Application Ser. No. 62/471,237, filed on Mar. 14, 2017, which is hereby incorporated by reference in its entirety.

TECHNICAL FIELD

The systems and methods disclosed herein are directed to biological sample collection and testing, and, more particularly, to a test kit for collecting oral fluid and detecting the presence and/or quantity of protective antibodies in the oral fluid.

BACKGROUND

Antibodies are proteins used by the immune system to neutralize foreign substances including bacteria, viruses, fungus, and animal dander, to name a few examples. Immunoglobulin (IgG) is the most common type of antibody found in circulation. An antibody can recognize and bind to a unique molecule of a specific foreign substance, called an antigen. Depending on the antigen, this binding may directly neutralize the foreign substance (for example, by impeding a biological process essential for its invasion and survival) or may tag the antigen so that other parts of the immune system destroy the foreign substance.

Antibodies are present in a biological fluid called serum that is typically obtained from blood. In blood, plasma is the liquid component that holds the blood cells in whole blood in suspension, and the serum is the component of plasma that is devoid of clotting factors. Serum includes other proteins not used in blood clotting, electrolytes, antibodies, antigens, hormones, and any exogenous substances (e.g., drugs and microorganisms). To obtain serum samples, blood is typically allowed to clot, and centrifuged to remove cellular components, yielding serum.

Seroprotection, the protection obtained from vaccination, can be estimated by analyzing samples of patient serum to determine whether protective levels of antibodies, such as immunoglobulins, are present in the serum. For many vaccines the amount of antibodies induced has a positive correlation with the likelihood of clinical protection from disease. Accordingly, mean antibody level is often used as a measure of vaccine efficacy, and seroprotection can be considered as an identified threshold level of antibody level that is correlated with protection from disease.

SUMMARY

In developing countries, the Expanded Program on Immunization (EPI), following guidelines promulgated by the World Health Organization, is responsible for immunizing infants younger than 12 months of age against a number of infectious diseases. These diseases include diphtheria, tetanus, pertussis, invasive Haemophilus influenzae type b (Hib) disease, hepatitis B, tuberculosis, pneumococcal disease, rotavirus gastroenteritis, and also yellow fever and encephalitis in some countries where disease incidence is particularly high. Some current EPI vaccines have had an enormous impact on diminishing mortality and morbidity from certain communicable diseases. For example, poliomyelitis due to wild type poliovirus has been eradicated since 1999 and wild type 3 poliovirus is nearing a similar fate, while measles mortality has been diminished drastically in some of the poorest countries of sub-Saharan Africa. Similarly, the burden of invasive Hib disease has been markedly reduced in multiple resource poor countries. These EPI successes constitute triumphs of preventive medicine.

Nevertheless, achieving and maintaining these public health advances represents a daunting and ongoing challenge. For example, demographic and health surveys, immunization coverage surveys, and administrative data often divergently estimate vaccination coverage, which hinders pinpointing regions where immunization services require strengthening. Three main methods are used to estimate success of a developing country's EPI in delivering vaccines to the targeted populations in different districts and regions: (1) administrative estimates, (2) coverage surveys, and (3) serosurveys. Administrative estimates of immunization coverage are based on the number of doses of vaccine administered in a target area and the number of individuals in the target population. These suffer from drawbacks due to often being based on inaccurate or old census data. Coverage surveys involve more precise field epidemiologic and statistical approaches to estimate the proportion of infants and toddlers who have received EPI vaccines. In a typical coverage survey, some sampling of households in a given region are selected, with the selected household having children in the target range, for example aged 12-23 months or 6-8 months. The coverage survey then sets out to assess immunization status of the children in the selected households through inspection of vaccination cards, immunization clinic records, and parental recall. However, these surveys do not readily identify smaller population sub-units where immunization coverage may be deficient, and further are subject to error when immunization records are not well kept and/or if parental reporting is inaccurate.

Serosurveys involve clinical analysis of antibody levels to provide objective immunologic evidence that the putatively vaccinated child (or adult) actually mounted immunologic responses and has serologic evidence of being protected. For these reasons, serosurveys constitute critical tools to assess, in greater depth, the quality of immunization services. Serosurveys also allow assessments at the population level of the proportion of the population that is protected against certain diseases, for example diseases that are the targets of regional elimination and/or control initiatives for global eradication.

The antibodies analyzed in serosurveys can be measured in serum, for example in venous blood serum, eluates of finger/heel stick blood that was dried and stored on filter papers, or in oral fluid specimens. Serum obtained from venous blood has been considered the "gold standard" clinical specimen for serology, however this requires centrifugation of blood samples after collection in order to obtain the needed serum and centrifugation is often impractical in the field. This creates requirements for temperature-controlled storage and transportation of blood samples, thereby increasing cost of testing and also removing the testing from the point of sample collection. Dried blood spot (DBS) samples can be obtained by pricking a finger or heel and placing drop(s) of patient blood onto a special filter paper to dry. DBS samples have advantages over venipuncture blood by not requiring centrifugation after collection and because DBS samples can be transported from the field at ambient temperature. However, DBS samples still typically require laboratory analysis, and also present risks in the form of puncture-site infection and contaminated needles.

Oral fluid can contain antibodies usable for serological testing. For example, in the sulcus or crevice located between the teeth and gums, there is a small amount of serum-derived fluid referred to herein as crevicular fluid. In healthy individuals, this fluid constitutes a transudate of plasma and is rich in immunoglobulin (IgG). Oral fluid specimens are desirable because they avoid the need for a "sharp" (e.g., a venipuncture needle or DBS lancet). Consequently, patient compliance is greater and in addition there are no resultant contaminated needles or lancets to be disposed of, thus reducing the exposure of health workers to sharps that may be contaminated with blood-borne pathogens (e.g., HIV, HBV or hepatitis C). Oral fluids, however, must be collected in a manner that ensures that they are enriched by the crevicular fluid that contains serum IgG that transudes into the crevice between the teeth and gums. If enriched by crevicular fluid, oral fluid titers can correlate closely with corresponding serum titers collected from the same tested patient to antigens such as tetanus toxoid, the measles virus, and Hib, to name a few examples.

For individuals with erupted teeth, oral fluid is collected at the gingival margin or within the gingival crevice to sample IgG derived from crevicular fluid. Edentulous (toothless) individuals, however, lack the gingival margin and gingival crevice from which to collect crevicular fluid. This can pose a problem for oral fluid serosurveys of infant children who may not yet have erupted any or many teeth. This can be compounded by the fact that the level of serum IgG present even in crevicular fluid-rich oral fluid is far lower than that present in venous blood serum, for example approximately 1% of the amount of IgG present in serum. Due in part to this lower concentration, oral fluid samples collected using existing devices are typically sent to a laboratory to undergo a centrifugation step before testing, adding significant delays to the testing process.

These and other problems are addressed in embodiments of the disclosed serological sampling system including a collection kit and detection device as described herein. The collection kit includes a swab that enables collection of oral fluid containing antibodies from both dentulous and edentulous individuals. For example, the swab can have a porosity or roughness that can abrade the oral mucosal epithelium to stimulate production of an immunoglobulin-containing mucosal transudate in edentulous individuals. Oral mucosal transudates are fluids from the capillaries beneath the buccal mucosa. The collection kit further includes a container that can be pre-filled with a solution, as well as a nozzle that a user can use to seal the sample in the container and compress the swab within the container. After or during compression, the container and nozzle can be inverted to flush the swab with the solution and to transfer the solution, now containing collected antibodies, to the detection device through a channel in the nozzle. The container, solution, and nozzle can cooperate to extract sufficient quantities of the collected antibodies from the swab for the detection system to be able to detect immunoglobulin levels indicative of seroprotection. In one non-limiting example, the detection system can be an assay reader device.

Beneficially, the disclosed serological sampling system avoids the centrifugation step necessary to obtain serum from venous blood, and thus is able to be used at the point of care for both sample collection and analysis. Further, the configuration of the disclosed serological sampling system can enable testing of oral fluid samples without the need for centrifugation. One or both of the collection kit and detection system can be hand-held, and together they can provide a rapid, reliable, and affordable system to test whether a patient has or does not have protective levels of antibodies against vaccine-preventable infections. Results from the disclosed serological sampling system can be used to objectively monitor the performance of immunization services, identify populations in need of immunization services, give objective immunization coverage information, provide estimates of the level of seroprotection of a population, and identify, even in the absence of detailed medical records, whether a patient has already received a particular immunization.

Accordingly, one aspect relates to a serological analysis system comprising a collection device comprising a tubular body having an interior volume comprising a primary interior volume having a lower surface and a well extending from the lower surface, an absorbent swab material configured to collect oral fluid containing antibodies from gums of a patient, a handle having a distal end coupled to the absorbent swab material, a proximal end spaced apart from the distal end, an elongate length extending therebetween, and a break point along the elongate length, an extraction solution in the tubular body, the extraction solution formulated to remove collected antibodies from the absorbent swab material, and a nozzle having a shaft, a channel extending centrally through the shaft, a plunger at one end of the shaft, the plunger having an exterior cylindrical surface, an interior cylindrical surface, and at least one planar surface joining the exterior cylindrical surface and the interior cylindrical surface, a plurality of radially extending channels formed in the at least one planar surface and the interior cylindrical surface, each of the plurality of radially extending channels forming a fluid path leading from the exterior cylindrical surface to the channel extending centrally through the shaft, and an elastomeric seal around the exterior surface of the plunger and configured to substantially seal the interior volume of the tubular body with the plunger inserted into the tubular body and the absorbent swab material positioned between the lower surface and the plunger; and a detection device comprising an assay test strip positioned to receive the extraction solution and collected antibodies from the channel of the nozzle, the assay test strip comprising at least one reaction zone configured to produce an optically-detectable change in appearance in the presence of the antibodies, an image sensor positioned to receive light reflected from the at least one reaction zone and configured to generate signals representing an intensity of the received light, and control electronics configured to analyze the signals and determine one or both of the presence and concentration of the collected antibodies in the at least one reaction zone.

In some embodiments, the plunger further comprises a rim along the exterior cylindrical surface forming a lowest surface of the at least one planar surface; and a plurality of protrusions around an aperture into the channel, the plurality of protrusions formed between portions of the plurality of radially extending channels. In some embodiments, each of the plurality of channels comprises a first segment formed as a groove in at least the rim, a second segment formed as a groove in a portion of the interior cylindrical surface of the plunger, and a third segment formed between two adjacent protrusions of the plurality of protrusions, wherein the first, second, and third segments form the fluid path leading from the exterior cylindrical surface to the channel extending centrally through the shaft.

In some embodiments, the break point of the handle is positioned along the elongate length such that the distal end of the handle, the swab material, and an intermediate portion extending along the elongate length between the swab material and the break point fit entirely within the interior volume of the tubular body. In some embodiments, the collection device is configured such that, in use, with the at least one planar surface of the plunger compressing the absorbent swab material against the lower surface of the interior volume, the distal end of the handle extends into the well.

In some embodiments, the absorbent swab material comprises an open-cell ester foam. In some embodiments, the open-cell ester foam has a porosity of 40 PPI to 60 PPI.

In some embodiments, the detection device comprises a network connection interface, and wherein the control electronics are configured to send data representing whether a pre-identified protective level of the antibody is in contact with the at least one reaction zone to at least one remote computing device over a network via the network interface.

In some embodiments, the assay test strip comprises a sample receiving zone for receiving the extraction solution and collected antibodies released through the channel of the nozzle; and a length of material extending between the sample receiving zone and the at least one reaction zone and configured to wick at least the extraction solution and collected antibodies from the sample receiving zone to the at least one reaction zone.

Another aspect relates to a fluid collection device comprising a tubular body having an interior volume comprising a primary interior volume having a lower surface and a well extending from the lower surface, a material configured to collect fluid, a breakable handle having a distal end coupled to the material, a solution in the tubular body, the solution formulated to remove particles in the collected fluid from the material, and a nozzle having a shaft, a channel extending centrally through the shaft, a plunger at one end of the shaft, the plunger having a plurality of radially extending channels formed in a bottom surface of the plunger, each of the plurality of radially extending channels forming a fluid path leading from an exterior cylindrical surface of the plunger to the channel extending centrally through the shaft, and a seal configured to seal the interior volume of the tubular body when the plunger is inserted into the tubular body.

In some embodiments, the plunger further comprises a rim along the exterior cylindrical surface forming a lowest surface of the bottom surface; and a plurality of protrusions around an aperture into the channel, the plurality of protrusions formed between portions of the plurality of radially extending channels. In some embodiments, each of the plurality of channels comprises a first segment formed as a groove in at least the rim, a second segment formed as a groove in a portion of an interior cylindrical surface of the plunger, and a third segment formed between two adjacent protrusions of the plurality of protrusions, wherein the first, second, and third segments form the fluid path leading from the exterior cylindrical surface to the channel extending centrally through the shaft.

In some embodiments, the breakable handle is shaped and sized such that a portion of the handle distal to a break location fits within the interior volume of the tubular body. In some embodiments, the device is configured such that, in use, with the bottom surface of the plunger compressing the material against the lower surface of the interior volume, the portion of the handle distal to the break location partially extends into the well.

In some embodiments, the material comprises an open-cell ester foam. In some embodiments, the open-cell ester foam has a porosity of 40 PPI to 60 PPI.

Another aspect relates to a method of testing seroprotection using oral fluid, the method comprising rubbing an absorbent swab material secured to a handle along the gums of a patient to collect oral fluid containing antibodies; inserting a portion of the handle, the absorbent swab material, and antibodies collected thereon into a tube having (i) a primary interior volume defined by an inner wall and a lower surface, (ii) a well extending from the lower surface, and (iii) a volume of extraction solution within the well and at least a portion of the primary interior volume; breaking the handle at a preformed break point such that a remaining portion of the handle having the absorbent swab material secured thereto fits within the tube; inserting a portion of a nozzle into the primary interior volume, the nozzle having a shaft, a channel extending longitudinally through the shaft, a plunger at one end of the shaft, the plunger having an exterior surface, an interior surface, and at least one additional surface joining the exterior and interior surfaces, a plurality of radially extending channels formed in the at least one additional surface and the interior surface, each of the plurality of radially extending channels forming a fluid path leading from the exterior surface to the channel extending longitudinally through the shaft; inverting the tube with the nozzle inserted partially into the tube and the absorbent swab material positioned within the primary interior volume; compressing the absorbent swab material between the lower surface of the primary interior volume and the at least one additional surface of the plunger; transferring a volume of the extraction solution from the channel of the nozzle to an assay test strip; inserting the assay test strip into an assay reader device; and based on an output of the assay reader device, identifying that the antibodies are present in the oral fluid.

In some embodiments, compressing the absorbent swab material causes a distal portion of the handle embedded within the absorbent swab material to extend into the well of the tube.

In some embodiments, inserting the absorbent swab material into the tube causes the absorbent swab material to absorb at least some of the extraction fluid. In some embodiments, compressing the absorbent swab material causes the absorbent swab material to express the absorbed extraction fluid, and wherein expressing the absorbed extraction fluid removes at least some of the antibodies collected on the absorbent swab material.

BRIEF DESCRIPTION OF THE DRAWINGS

The disclosed aspects will hereinafter be described in conjunction with the appended drawings and appendix, provided to illustrate and not to limit the disclosed aspects, wherein like designations denote like elements.

DETAILED DESCRIPTION

Introduction

Figure 1:
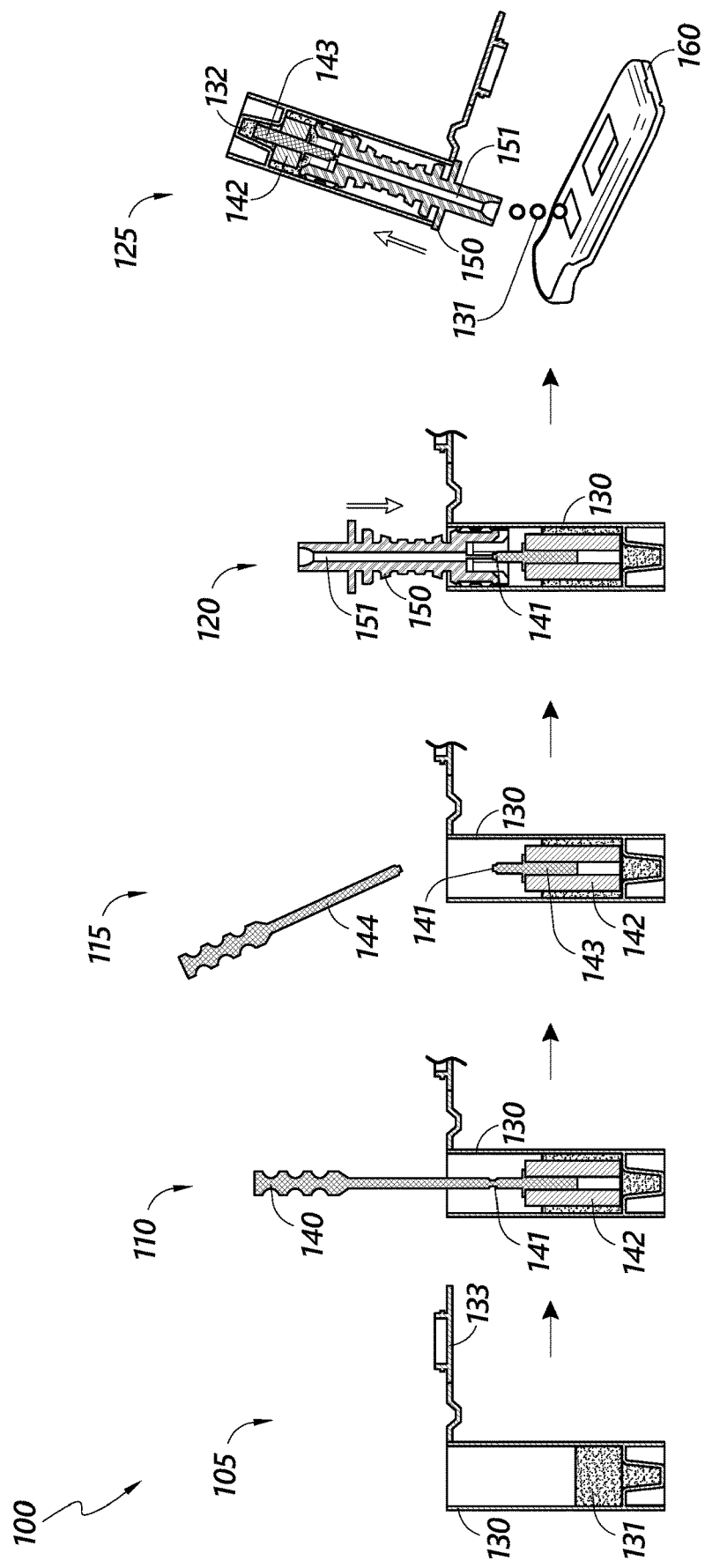
FIG. 1 graphically illustrates steps of an example method of using a serological fluid collection device as described herein.

Embodiments of the disclosure relate to systems and techniques for detection of seroprotection. A serological sampling system for seroprotection testing can include (1) a collection device for collecting gingival crevicular fluid and oral epithelial, mucosal transudates; and a (2) testing device for detecting the presence and/or quantity of specific antibodies in the collected fluid. Throughout this disclosure, example systems, kits, and methods will be described with reference to collection, testing, and detection of antibodies, but it will be understood that the present technology can be used to collect, test, and detect any particle, molecule, or analyte of interest.

A collection device can include a swab, a container, and a nozzle for compressing the swab in buffer solution after collection of the oral fluid. The swab can be constructed from a special material having desired abrasiveness, pickup efficiency, and shedding efficiency for detecting required amounts of antibodies, for example an open-cell foam. The swab can be provided on a handle. The user can use the swab and handle to collect oral fluid samples from a patient. After swabbing the mouth of the patient, the user places the swab into the container. The handle may include a break point so that the user can break off the swab by angling the handle against the side of the container without physically contacting (and thus contaminating) the swab. A liquid, for example an extraction solution, can be provided within the container. The swab absorbs the extraction solution when it is placed in the container. The user can insert the nozzle into the container to compress the swab to express absorbed extraction solution and any collected antibodies, and the nozzle can include a fluid path that dispenses the expressed fluid onto a test device. The structure and fluid path of the nozzle can be designed to collect solution expressed from the exterior surface of the swab where antibody concentration is likely to be highest.

One suitable detection system includes an immunoassay device. Immunoassay devices play an important role in areas such as clinical chemistry and have been made portable for use in the field. Immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones. The analyte of interest is generally detected by reaction with a capture agent, which yields a device more easily detected and measured than the original analyte. Detection methods can include a change in absorbance, a change in color, change in fluorescence, change in luminescence, change in electrical potential at a surface, change in other optical properties, or any other easily measured physical property indicating the presence or absence of an analyte in a sample.

As described above, the disclosed serological sampling systems can beneficially enable seroprotection testing in the field, for example but not limited to for assessment of EPI immunization programs. Thus, the detection systems can be configured for identification of concentrations of antibodies that would be present in patient serum after receiving one or more EPI immunizations, for example pentavalent vaccine, measles vaccines, and poliovirus vaccines. Specific information relating to testing of the antibodies that evidence immunization with such vaccines is presented in more detail below, and it will be appreciated that the disclosed serological sampling systems can be adapted for testing of other antibodies or analytes of interest. It will also be understood that the disclosed serological sampling systems can be beneficial to test seroprotection in any context, including point of care facilities like doctor's offices, hospitals, pharmacies that offer immunization programs, and urgent care facilities, as well as in healthcare situations where the medical records of a patient are not available.

Antibody titers to three sets of antigens—tetanus, invasive Haemophilus influenzae type b disease (Hib), and hepatitis B virus (HBV)—can be particularly helpful in providing objective information to document that infants and toddlers have been immunized with pentavalent vaccine. The disclosed serological analysis systems can be used to collect and analyze serum for antibody titers to one or more of these three antigens in various implementations. Among these three serologic assays, the measurement of tetanus antitoxin can provide advantages as it can be used equally well in surveys of both toddlers 12-23 months of age and in infants 6-8 months of age to provide objective evidence regarding efficacy of vaccination programs, for example but not limited to EPI services.

As an example, protective titers of tetanus antitoxin in toddlers 12-23 months of age can provide objective evidence of immunization with pentavalent vaccine. A level of 0.01 IU/ml of neutralizing tetanus antitoxin in serum may be considered a protective level of the neutralizing tetanus antitoxin. Because the amount of IgG in properly collected oral fluid (e.g., oral fluid that is rich in crevicular fluid) from an individual may be only 1% of that subject's serum IgG level, some embodiments can use the detection of 0.0015 IU/ml of tetanus antitoxin in oral fluid as the proxy for identifying an individual with a serum tetanus antitoxin titer of >0.15 IU/ml. Some embodiments can use levels of as low as 0.0002 IU/ml of tetanus antitoxin in oral fluid as a seroprotective threshold. As another example, in the much younger and more restricted age group of infants 6-8 months of age, the demonstration of high (>1.0 mcg/ml) titers of IgG antibody to polyribosyl ribitol phosphate (PRP), the polysaccharide that encapsulates Hib, constitutes strong evidence of immunization with at least two doses of Hib conjugate vaccine, as contained within the pentavalent combination vaccine. PRP antibodies are less useful in toddlers because by that age the antibodies may derive from natural exposure to Hib (or other bacteria bearing antigens related to PRP) rather than from immunization. By contrast, in infants 6-8 months of age, measurement of high titers of anti-PRP can be very useful in ascertaining pentavalent immunization status. In some implementations, the cut-off of 0.01 mcg/ml of PRP antibody in oral fluid can be used for determining vaccine-derived antibody in 6-8 month old infants. Measuring antibodies against HBV surface and core proteins is the third serologic method of assessing whether children received pentavalent vaccines as infants. Some embodiments can use levels of 0.12 IU/ml of HBV surface proteins in oral fluid as a seroprotective threshold. The presence of HBVs antibodies in the absence of HBVc antibodies differentiated vaccines from children infected with wild type HBV.

Another useful serological measurement involves the measles antibody. The disclosed systems can be used to collect and test serum samples for the measles antibody in some implementations. If they were immunized with measles vaccine at 9-12 months of age, around 96-98% of toddlers 12-17 months of age will manifest protective titers of measles IgG. However, if the measles vaccine was not properly maintained (e.g., inadequate cold chain), this will be signaled by a low prevalence of protective antibodies. Moreover, approximately 2-3% of infants fail to seroconvert after their initial immunization with measles vaccine. Two levels of measles PRN antibodies in oral fluid, 1.2 mIU/ml and 2.0 mIU/ml, can be used in various implementations as the seroprotective threshold.

Additionally, with the global diminution of countries having ongoing active transmission of type 1 polio to a small number, there is a need for a practical test to detect protective levels of IgG poliovirus antibodies in the individual subject and the prevalence in populations. The disclosed systems can be used in some implementations to test for protective levels of IgG poliovirus antibodies.

The disclosed systems can be capable of detecting at least the above-described identified protective levels of specific gold standard titers (neutralization assays) and IgG ELISA titers, and in some embodiments can detect a level of seroprotection expressed as a percentage of an identified target level (e.g., 30%, 50%, 70%, etc.).

Various embodiments will be described below in conjunction with the drawings for purposes of illustration. It should be appreciated that many other implementations of the disclosed concepts are possible, and various advantages can be achieved with the disclosed implementations.

Overview of Example Collection Method

FIG. 1 graphically illustrates steps of an example method 100 of using a serological fluid collection device as described herein. The example method 100 can be used to collect serological fluid from an individual and measure the level of seroprotection of the individual, for instance based on the antibodies and associated seroprotective levels described above in some implementations. Prior to method 100 beginning, an oral fluid specimen is collected from an individual using the swab 142 described below. The specimen can be collected using a specified collection protocol. The oral fluid specimen can be collected using a swab described in detail below. As used herein, oral fluid can refer to a fluid obtained by sampling the mouth of a patient, where the fluid includes crevicular fluid and/or mucosal transudates and may have some admixture with saliva.

The method 100 begins at step 105, in which a user opens a cap 133 of a tube 130 filled with an extraction solution 131. The tube 130 can be pre-filled in some embodiments, or the user can fill the tube 130 with the desired amount of solution 131. In some embodiments this can be around 350 µL of fluid, however this volume can be varied based on the requirements of the associated test system, the volume of swab material being eluted (as described below), and the desired sample concentration, to name a few examples. In some embodiments the volume can be in a range between 300 µL and 400 µL of fluid. Prior to opening the cap 133 in some pre-filled embodiments the user can hold the tube 130 vertically and gently tap it to make sure that all of the solution 131 is in the bottom of the tube 130. The composition of the extraction solution 131 can be varied to accommodate solubilizing and diluting various antibodies, and can include buffer, preservative and other ingredients.

The volume of extraction solution 131 can be selected to provide saturation and elution of the swab 142 to flush the collected antibody from its surface(s). For example, use of larger or smaller volumes of fluid (relative to the volume and/or absorbent properties of the swab 142) can affect the amount of recovered antibody. If the volume of solution 131 is too small, all of the antibody on the swab 142 may not be eluted but the antibody concentration dispensed into the test device is higher. Larger volumes can completely (or substantially completely) wash the collected antibody from the swab 142, however the antibody concentration dispensed into the test system will be lower.

The volume of extraction solution 131 can additionally or alternatively be selected to provide a sufficient amount of fluid for capillary flow along a test strip as described herein. For example, one embodiment of a test strip used with the disclosed collection device can use 100 µL of fluid to achieve sufficient capillary flow to move a sample from a receiving zone to a test zone, and a minimum volume identified for reliably delivering 100 µL to the testing device can be around 350 µL due to some liquid remaining in the swab 142 after compression and some liquid remaining in the tube 130 and/or nozzle 150 (discussed below). As some test systems measure concentration and not total mass, the volume of solution 131 can reflect a balance between flushing the collected antibody from the swab 142, achieving a desired volume of output fluid, and achieving a desired concentration of antibodies in the output fluid. Similarly, in some embodiments the volume and/or absorbent properties of the swab 142 can be determined at least partly based on the desired output volume and concentration for a particular test system.

For example, the volume of extraction solution 131 and/or the absorbent properties of the swab 142 can be optimized to obtain a desired assay sensitivity. One variable that can be optimized to maximize the observed assay sensitivity is the amount of analyte of interest that is extracted from the swab 142 and applied to the assay. The amount of extracted analyte of interest can be increased by applying an increasing amount of extraction solution 131 to and through the swab 142. As the amount of extraction solution is increased to achieve maximum analyte extraction, however, the analyte of interest is progressively diluted in the extraction solution and, in some cases, may become so diluted that assay sensitivity is decreased or degraded (potentially rendering the test inoperable). In one non-limiting example, a volume of diluent, for example extraction solution 131, is selected to maximize the amount of analyte (for example, collected antibody) extracted from the swab 142 while also ensuring that the analyte of interest is not diluted to such an extent that observed assay sensitivity is reduced. In one non-limiting example described above, optimal observed assay sensitivity is obtained when about 350 µL of extraction solution 131 is used to extract about 100 µL of an oral fluid sample captured on the swab 142. Optimal results may also be obtained with different volumes of extraction solution 131 and with different swab dimensions and liquid absorption capacity. In one non-limiting implementation, a 1:4 or 1:5 dilution ratio of oral fluid sample volume to extraction solution volume achieves optimal observed assay sensitivity.

At step 110, the user can insert a swab 142 on a handle 140 into the tube 130 and into the solution 131, and the swab 142 can absorb some or all of the solution 131. The handle 140 can have a break point 141 along its length and positioned such that, when the swab 142 is contacting or near the bottom surface of the tube 130, the break point 141 is within the tube 130.

At step 115 the user can break the handle and leave a portion of the handle and the swab 142 in the tube 130. In one non-limiting example, the user can apply pressure to a proximal portion 144 of the handle 140 to break the handle 140 at the break point 141. The proximal portion 144 can be discarded while an intermediate portion 141 remains within the tube 130 with a distal portion 143 embedded within the swab 142. As used herein, "proximal" and "distal" are used to describe structures from the perspective of the user, where "proximal" refers to the end of the handle 140 closest to the user and "distal" refers to the end of the handle farthest from the user.

At step 120, the user can insert a nozzle 150 having an interior channel 151 into the tube 130, for example until o-rings or a sealing element engages and seals the tube.

At step 125, the user can transfer fluid 131 to a cartridge 160 containing a test strip, or to another test device. For example, the user can compress the swab 142 by pushing the nozzle 150 into the tube 130 such that the distal portion 143 of the handle extends into a well 132 of the tube 130. This can allow the user to flush the collected sample from the swab and to drip fluid from the nozzle channel 151 onto a sample receiving zone of a test strip within a cartridge 160 (e.g., the portion of the test strip below the illustrated shallow well located on one end of the cartridge 160). As described above, the fill volume of the fluid 131 within the tube 130 can be selected such that, when all of the fluid is expelled with reasonable compression force, the volume dispensed onto the test cartridge is about 100 µL. Other dispense volumes can also be suitable and readily achieved using embodiments of the devices described herein.

The test strip within the cartridge 160 can include one or more test zones each configured to bind to a specific antigen and produce an optically-detectable change indicative of the presence and/or concentration of the antigen. The test strip can also include a control zone used to monitor that reagent addition and fluid flow across the test strip have occurred properly. This serves as an indicator that the assay steps have been performed correctly by the operator, a built-in control step that is beneficial when such a device will be used in the field. Thus, the cartridge 160 can have a window exposing these portions of the test strip to the user or a reader device.

As illustrated, the tube 130 and nozzle 150 can enclose the swab 142. This can be beneficial relating to disposal after testing. For example, the swab 142 and any collected oral fluids remaining on the swab can be disposed of together, substantially sealed within the tube 130 and nozzle 150. This can help mitigate the risk of exposure of healthcare personnel to any potential pathogens also collected with the oral fluid.

In some embodiments, the test strip can be an assay, for example a triplex assay configured to provide indication of protective levels of IgG antibodies to vaccine antigens of interest, for example i) tetanus toxin protein, ii) measles virus antigen, and iii) type 1 poliovirus antigen. As another example, the assay can be a monoplex test configured to provide indication of IgM measles antibody as a diagnostic test for recent (acute) infection with measles virus.

Though not illustrated, further steps can include inserting the cartridge into a reader device, operating the reader device to perform imaging and analysis of the test strip, and viewing results of the test. The testing device can be an immunoassay reader, for example a lateral flow assay and reader device, with an interface that alerts the user to the presence and/or degrees of seroprotection of the tested sample. Fluid can be released from the container onto a receiving zone of an assay test strip in some embodiments. The assay test strip can then be inserted into a reader to image the indicators on the strip, analyze the image(s), determine a level of seroprotection, and report the determined level of seroprotection to the user. The reader can have more than one method of entering data regarding the sample and can have various ways of saving, storing, displaying, uploading and alerting the appropriate personnel of detected results.

Although the disclosed detection devices are typically described herein with reference to test strips and lateral flow assay reader devices, it will be appreciated that the described seroprotection detection aspects described herein can be implemented in any suitable detection system. For example, features described herein can be implemented in reader devices that analyze other types of assays, such as but not limited to molecular assays, and provide a test result. Some embodiments of the detection devices can use a chromatographic sandwich or immunoassay in lateral flow format for the qualitative/semi-quantitative detection of target analyte(s) in a sample. Further, the collected fluid can be transferred to a centrifuge, spectrometer, chemical assay, or other suitable test device to determine the presence and/or concentration of one or more antibodies in the sample.

Overview of Example Serological Collection and Detection Systems

FIGS. 2A-2D illustrate various views of an example serological fluid collection device container 200. The container 200 includes a tube 215 and a cap (variations designated as 205A, 205B).

Figure 2A:
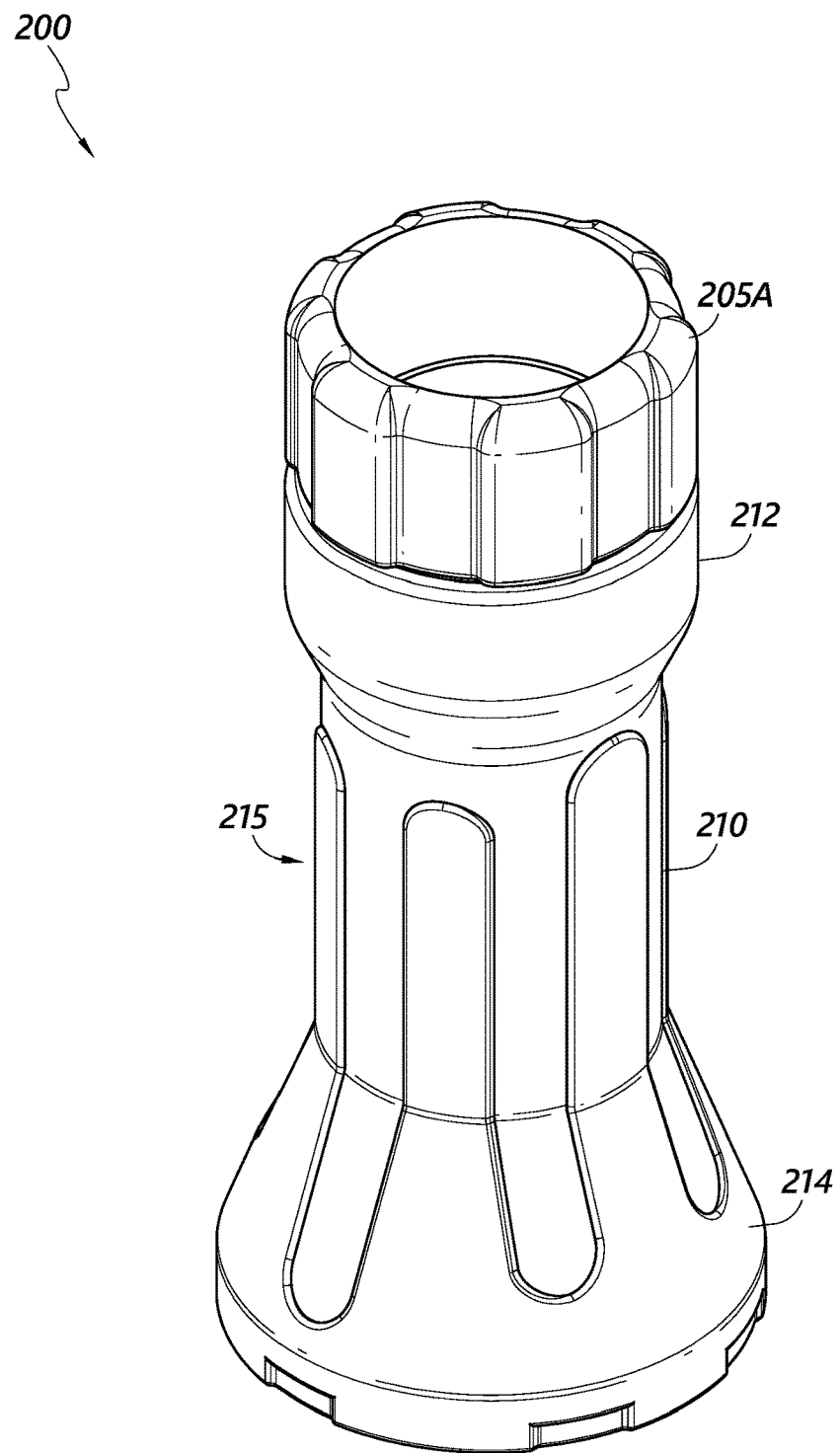
FIGS. 2A-2D illustrate various views of an example serological fluid collection device container.

FIG. 2A illustrates a perspective view of the collection device container 200. As illustrated, the tube 215 includes a central body 210, a receiving portion 212, and a base portion 214. The receiving portion 212 can be flared outward, e.g. have a larger circumference than the central body 210, to facilitate insertion of a swab as described herein. The base portion 214 can similarly be flared outward. The larger circumference of the base portion 214 relative to the central body 210 can provide a more stable base and prevent inadvertent tipping when the container 200 is set upright on a surface. The cap 205A can create a fluid-tight seal with the receiving portion 212 of the tube 215.

Figure 2B:
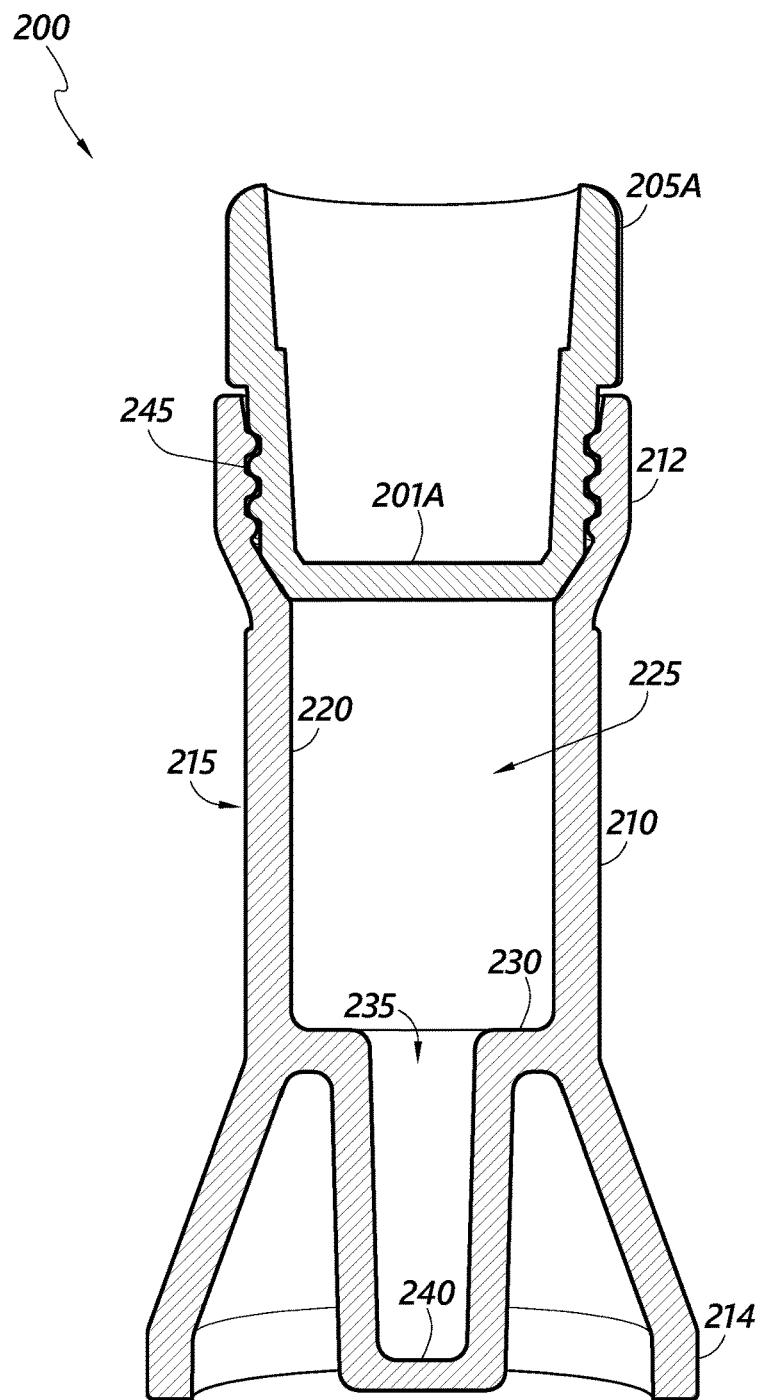

FIG. 2B illustrates a cross-sectional view of the collection device container 200. The receiving portion 214 can include interior threads 245 that engage exterior threads on a lower portion of the cap 205A. The view of FIG. 2B depicts the threads 245 used to secure the cap 205A to the tube 215 in this embodiment, as well as how a sealing surface 201A of the cap 205A is positioned within the tube 215. Other mechanisms to couple the cap 205A and the tube 215 in a way that forms a fluid-tight seal are suitable. For example, it will be appreciated that alternate embodiments of the cap 205A can be press-fit within the tube 215 to create the seal, o-rings can be provided on the cap 205A or in the receiving portion 214, or the threads 245 can be positioned on the exterior of the receiving portion 212 and engage interior threads of the cap 205A. In one non-limiting embodiment, a shoulder on the bottom of the cap can engage a ledge on the receiving portion 212 to help form and maintain a fluid-tight seal. The fluid-tight seal between the cap 205A and the tube 215 allows the tube 215 to be pre-filled with a desired volume of solution in a controlled environment, for example in sterile conditions in a manufacturing facility, and to maintain that seal during storage until the container 200 is used for testing.

As shown in FIG. 2B, the base portion 214 can form a support wall, for example a conical, cylindrical, or other wall. Such a wall can save material by providing a supportive circumference without a solid bottom surface. In other embodiments the tube 215 can additionally have a generally planar bottom surface that is bounded by the outer circumference of the base portion 214.

The central body 210 of the tube 215 can be a tubular body that includes a cylindrical interior wall 220 and lower surface 230. The lower surface 230 defines a primary interior volume 225 of the tube 215 for receiving a swab as described herein. An additional volume 235, referred to herein as a "well," extends below the lower surface 230 of the primary interior volume 225 to a lowest interior surface 240 of the tube 215. This well can be sized with a diameter and length sufficient to receive all (or substantially all) of the portion of a rigid handle embedded within a swab so that the swab can be compressed against the lower surface 230. The diameter of the cylindrical interior wall 220 can be approximately equal to the diameter of the swab in some embodiments.

Figure 2C:
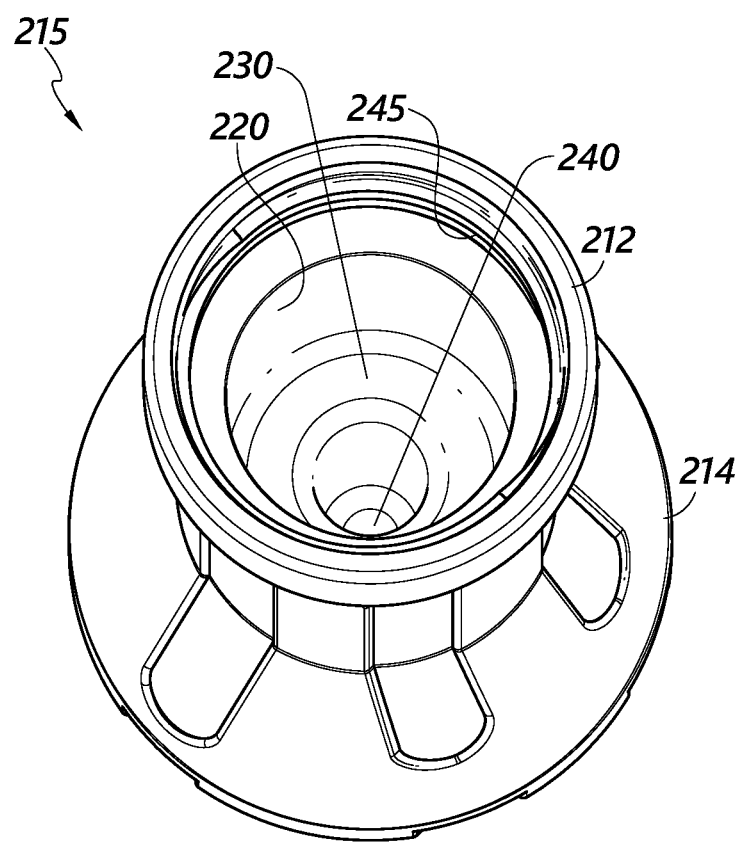

FIG. 2C illustrates a top perspective view of the tube 215, showing the stepped interior leading from the largest diameter at the receiving portion 212 to the intermediate diameter of the interior wall 220 of the central body 210 to the smallest diameter of the well 235. The lower surface 230 of the primary interior volume 225 of the central body 210 and the lowest interior surface 240 of the well 235 are also visible in the view of FIG. 2C.

Figure 2D:
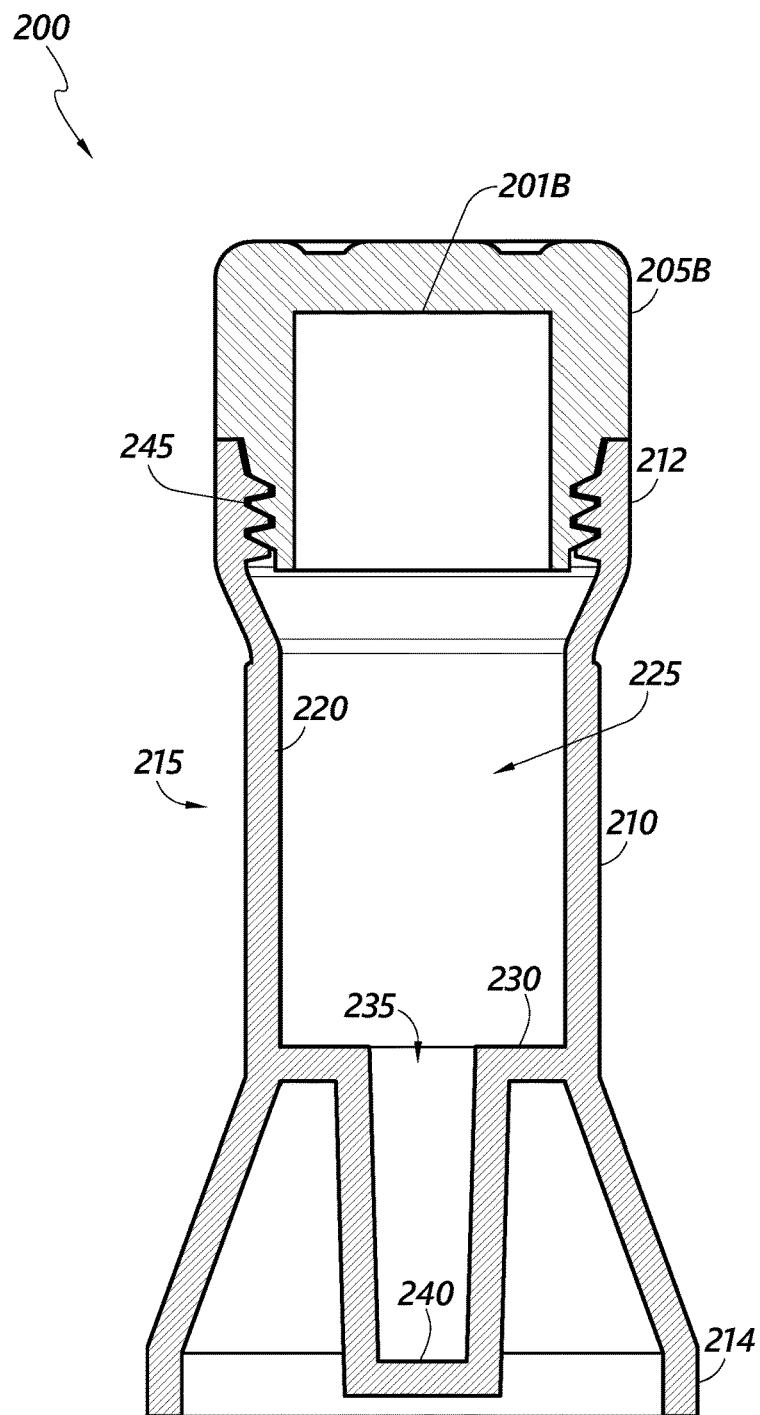

FIG. 2D illustrates a cross-sectional view of the collection device container 200 having an alternate cap 205B. The sealing surface 201B of the cap 205B that encloses the interior volume of the tube 215 is positioned at the top of the cap 205B, thereby allowing for a larger interior volume than the example container 200 including cap 205A.

Figure 3A:
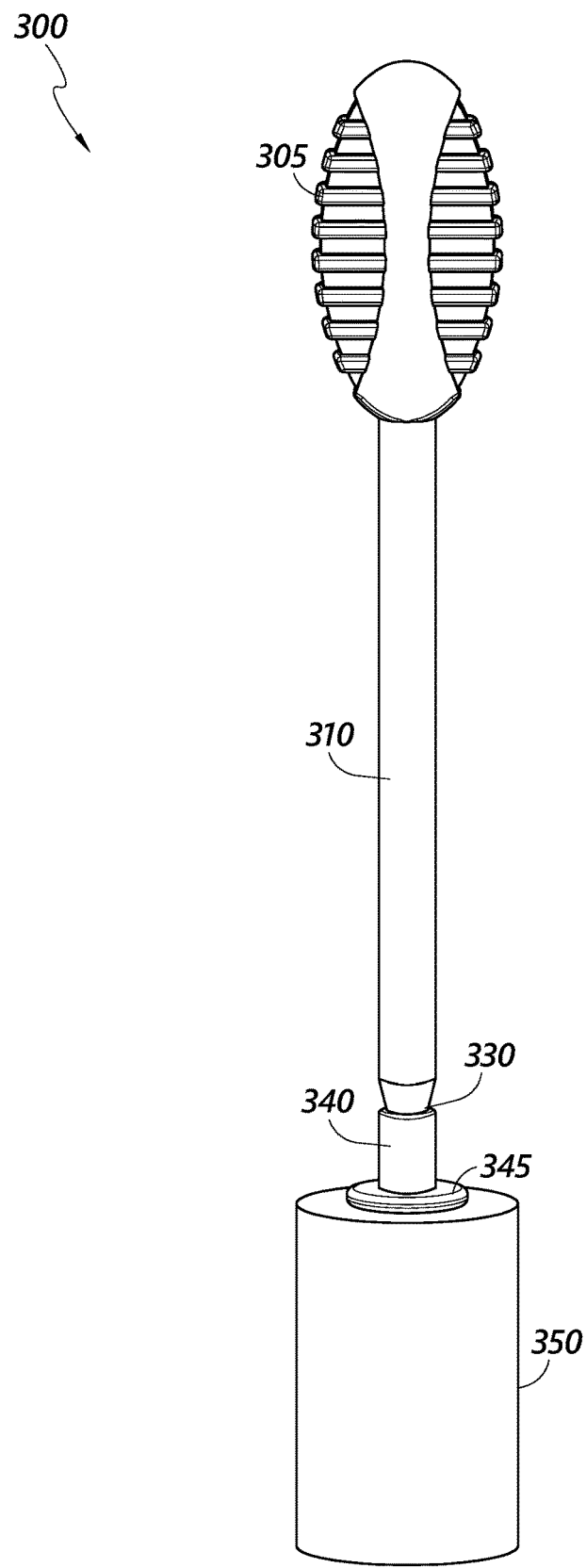
FIGS. 3A-3C illustrate various views of an example serological fluid collection device swab.
Figure 3B:
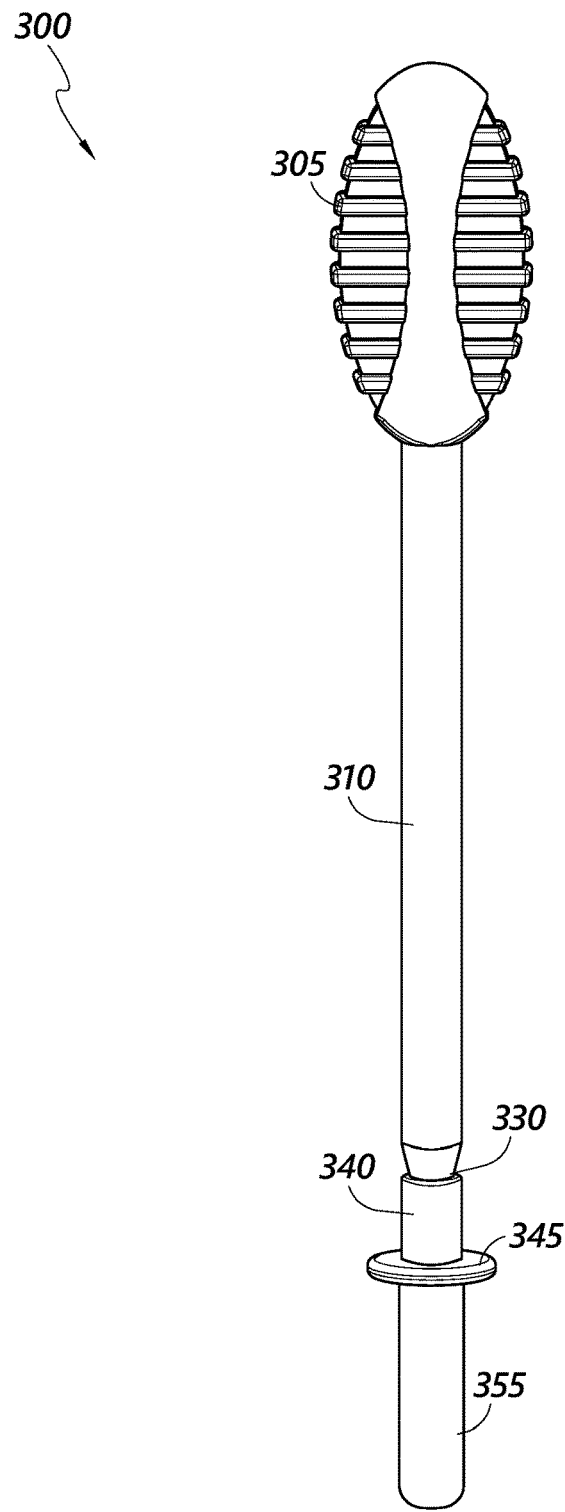
Figure 3C:
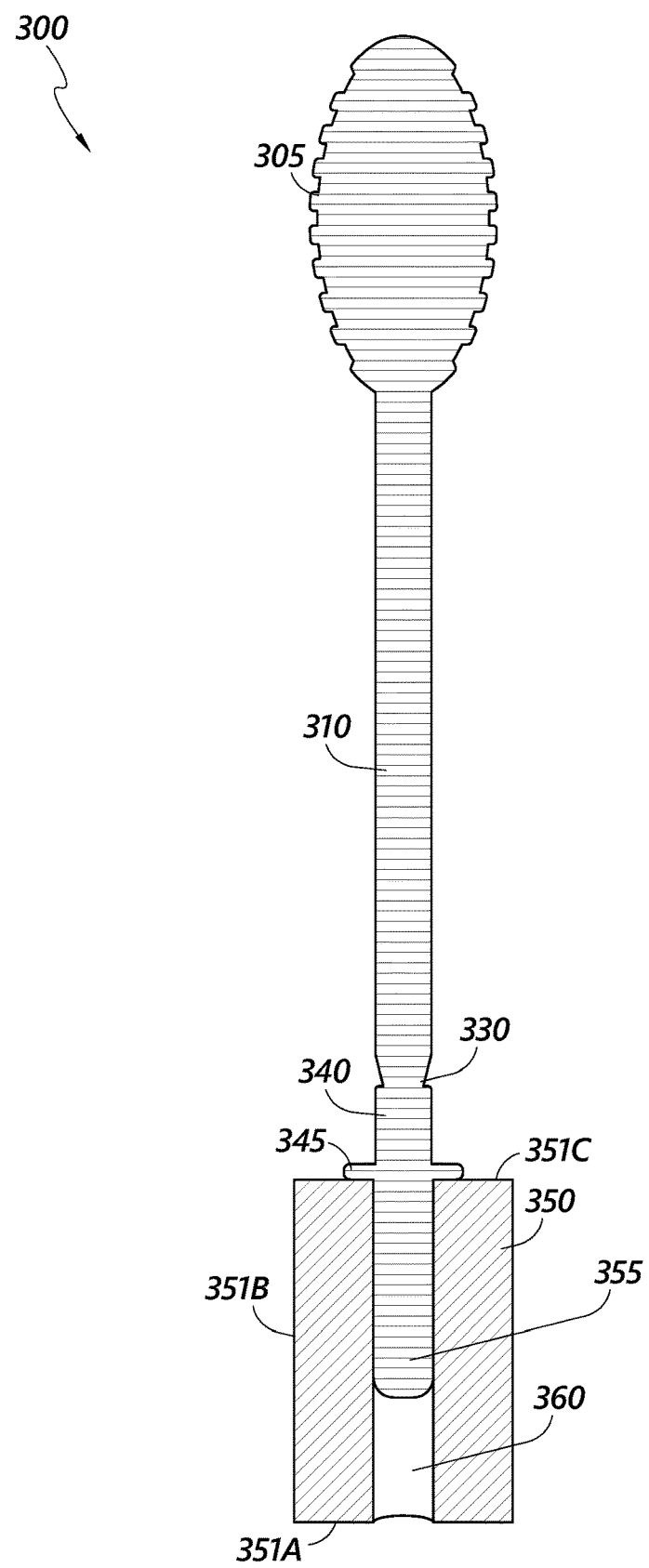

FIGS. 3A-3C illustrate various views of an example serological fluid collection device swab 300. The swab 300 includes a handle 310 and a swab material 350 attached to a distal end of the handle 310. FIG. 3A depicts a front view of the swab 300, FIG. 3B illustrates another front view with the swab material 350 shown in transparency, and FIG. 3C illustrates a cross-sectional view of the swab 300. FIGS. 3A-3C are discussed together below.

The swab material 350 can have an internal channel or aperture 360 for securing to the handle 310. This channel can extend completely through the length of the swab material 350 to allow the swab material 350 to compress against the flange 345, with the distal surface of the swab material 350 pushed proximally toward the flange by lower surface 230 of the container 200 while the rigid distal portion 355 of the handle 310 extends into the well 235. The swab material 350 can compress along a longitudinal axis of the distal portion 355 of the handle during sample extraction, as described in detail below.

The handle 310 in this embodiment includes a grip 305 on a proximal portion of the handle 310, a break point 330, a flange 345 positioned against an upper surface of the swab material 350, an intermediate portion 340 extending between the break point 330 and the flange 345, and a distal portion 355 embedded within the swab material 250.

As illustrated, the grip 305 can have a larger cross-section than the handle shaft and include ridges and grooves to facilitate grip by a user. Other grips or no grip can be used in other implementations.

The break point 330 can be formed as a reduced cross-section of the handle shaft, and can be positioned close enough to the distal end of the handle such that, when the handle is inserted within a collection kit tube (e.g., tube 215), the break point is within the internal volume of the tube. Thus, after a user breaks the proximal portion of the handle at the break point 330, the remaining portion of the handle can be enclosed within the tube by a nozzle as described in detail below. The reduced cross-section of the break point 330 can be large enough to withstand forces incident upon the handle 310 when a user obtains a sample on the swab material 350, but small enough to be snapped or broken easily with a single hand of the user. The break point 330 of the handle can be positioned along the elongate length of the handle such that the distal portion 355 of the handle, the swab material 350, and the intermediate portion 340 extending along the elongate length between the swab material 350 and the break point 330 fit entirely within the interior volume of the tubular body of a container, for example container 200.

The flange 345 can be a substantially flat circular, rectangular, or other shaped structure to support the swab material 350 during sampling and prevent the swab material 350 from being pushed from the distal end of the swab 300 along the handle 310 toward the proximal end of the swab 300. The flange 345 can be shaped and sized to fit inside a recessed portion in a bottom of the plunger, for example in a recessed portion formed by a rim 455 and intermediate sections 460 of a plunger 400 discussed in detail below with reference to FIG. 4F. In this example, the diameter of the flange 345 can be slightly less than the interior diameter of the recessed portion. In this example, the diameter of the flange 345 can be slightly less than the interior diameter of the recessed portion.

The distal portion 355 of the handle 310 can provide structural support to the compressible swab material 350 during sample acquisition, allowing a user to gently abrade the gums and/or press the swab material 350 into the gingival crevice. The distal portion 355 of the handle 310 can be adhered to the swab material 350 in some embodiments, and in some embodiments can have barbs to extend into a portion of the aperture 360 of the swab material 350 to secure the material 350 on the distal portion 355. In some cases, however, this attachment is along the upper surface of the swab material adjacent to the flange 345 to allow for axial compression of the swab material along the longitudinal axis of the distal portion 355 during compression within a tube 215 as described herein. Compression of the swab material 350 along the longitudinal axis of the distal portion 355 can cause the distal-most end of the handle to translate completely through the aperture 360 and past the distal-most end of the swab material 350. As will be described in detail below, the distal portion 355 of the handle 310 that extends past the distal-most end of the swab material 350 during compression can engage a feature in a tube (such as well 235 in tube 215). Thus, during such compression, the distal portion 355 of the handle 310 can extend into the well 235 of the tube 215 while the swab material 350 is compressed against the lower surface 230.

The swab material 350 can be saturated with crevicular fluid and/or oral mucosal transudates by rubbing the swab along the junction of the teeth and gums for a predetermined time, for example approximately 1 minute. For edentulous individuals and young infants with few erupted teeth, the swab can be rubbed along the gums to stimulate production of oral mucosal transudates. Thus, the swab 300 is able to obtain IgG-rich oral fluid from adult and pediatric subjects in a simple, non-invasive manner. In some aspects, the exposed lower outer surface 351A and outer circumferential surface 351B of the swab material 350 can primarily collect the oral fluid during sampling.

Desirably, the swab material 350 is absorptive, compressible, abrasive, and low-protein-binding. For example, the swab material 350 can be absorptive enough to absorb around 350 μL of fluid and sufficiently compressible to release substantially all of the absorbed fluid. In some examples, the swab material 350 can be foam, for example open-cell ester foam. The foam swab material can be polyester polyurethane foam, for example 2.0C Polyester Polyurethane Foam from United Foam®. In some implementations the foam can be impregnated with ingredients that enhance the absorption of crevicular fluid and help preserve the fluid.

In cases where the swab material 350 is an open-cell foam or other porous material, the material will include pores. The edges of the foam pores can scrub the gums to stimulate production of oral mucosal transudates as described above to obtain antibodies even in the absence of teeth, and thus foam porosity can relate to the ability of the foam to obtain the required samples. The foam can have an average pore size around 1 mm in diameter in some embodiments, and such a pore size can achieve the desired abrasiveness. Other embodiments can have a pore size between 0.25 mm (corresponding to around 100 PPI) and 1 mm (corresponding to around 25 PPI). During testing, foam with 100 pores per inch (PPI) was well tolerated by subjects, but this foam did not sufficiently abrade the gum tissue to collect an adequate IgG sample. Foam with 50 PPI porosity is moderately abrasive but still tolerated by subjects. Below around 30 PPI porosity, foam can become very abrasive, and porosities lower than about 20 PPI can compromise the strength of the foam as it is mostly pores and does not include much supporting foam material. Thus, in some embodiments a range of 20 PPI to 80 PPI is preferable, and in some embodiments a range of 40 PPI to 60 PPI is most preferable. In order to mitigate bonding with the sampled antibodies, the swab material 350 can be hydrophilic, as hydrophobic materials may bond non-covalently to hydrophobic portions of antibody proteins.

FIGS. 4A-4G illustrate various views of an example serological fluid collection device nozzle 400. The nozzle 400 includes a shaft 405, a grip 410 extending from an intermediate portion of the shaft 405, and a plunger 415 configured to sealingly engage a serological fluid container (e.g., container 200) during compression of a swab material (e.g., swab material 350). The nozzle can be formed as a unitary component, for example by injection molding a suitable plastic.

Figure 4A:
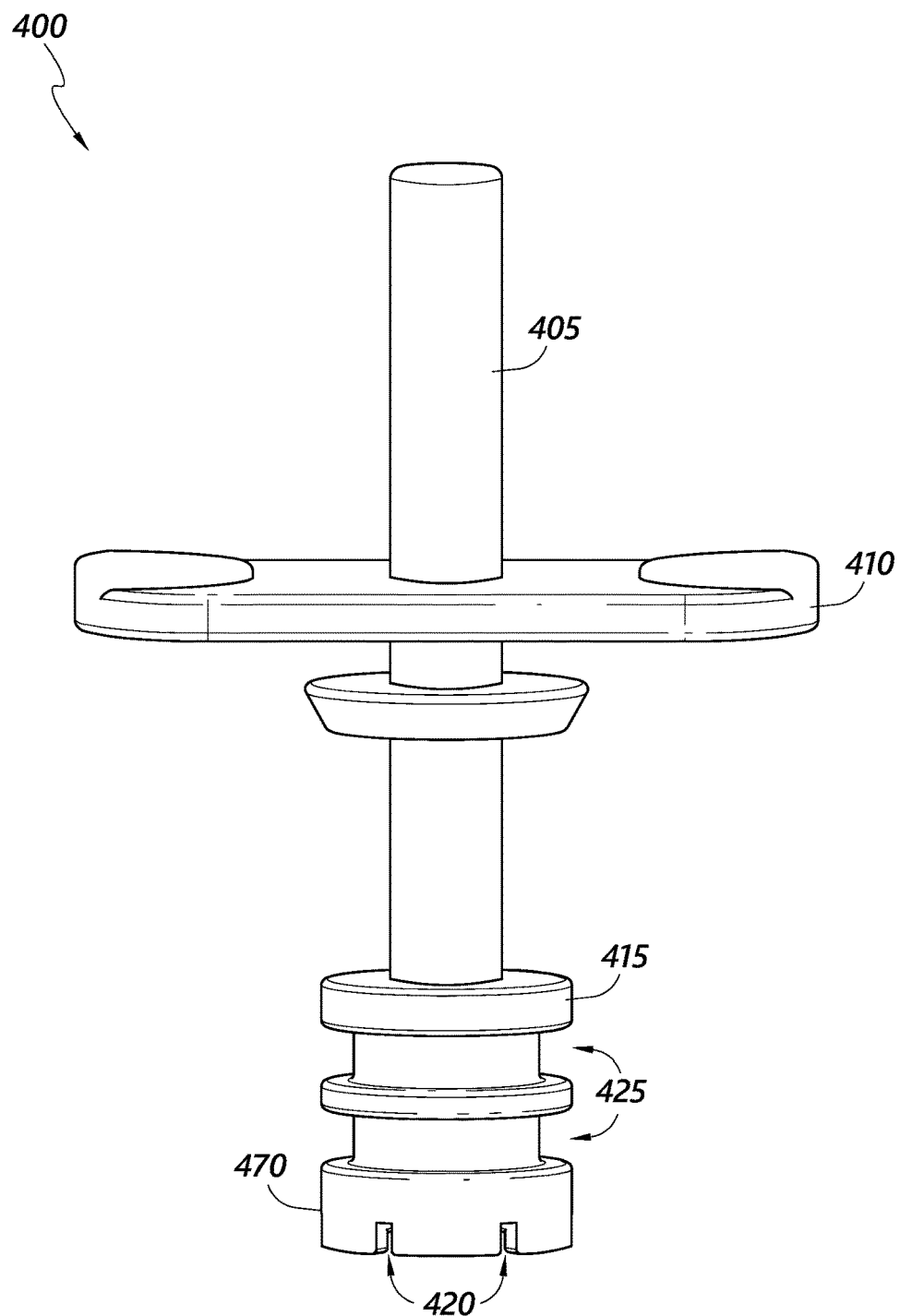
FIGS. 4A-4G illustrate various views of an example serological fluid collection device nozzle.

FIG. 4A depicts a front view of the nozzle 400, illustrating the shaft 405, grip 410, and plunger 415. The grip 410 can be a rigid member extending approximately perpendicularly to the shaft 405 and sized to permit a user to grip the nozzle with at least one finger on each side of the shaft 405 and apply pressure to draw the nozzle 400 inward into a container 200. The nozzle 400 can translate along a longitudinal axis of the container 200 to seal the swab material 350 within the container 200 and to compress the swab material 350 within the container 200. The size and/or shape of the grip 410 can be varied in other embodiments. The plunger 415 can be provided at one end of the shaft 405 and can have one or more recesses 425 for retaining an elastomeric sealing member, for example an o-ring. An outer circumference of the plunger 415 can be sized to slide within the inner wall 220 of the container 200 with the sealing members engaged with the wall 220. The plunger 415 can also have a plurality of radially extending channels 420 as discussed in more detail below.

Figure 4B:
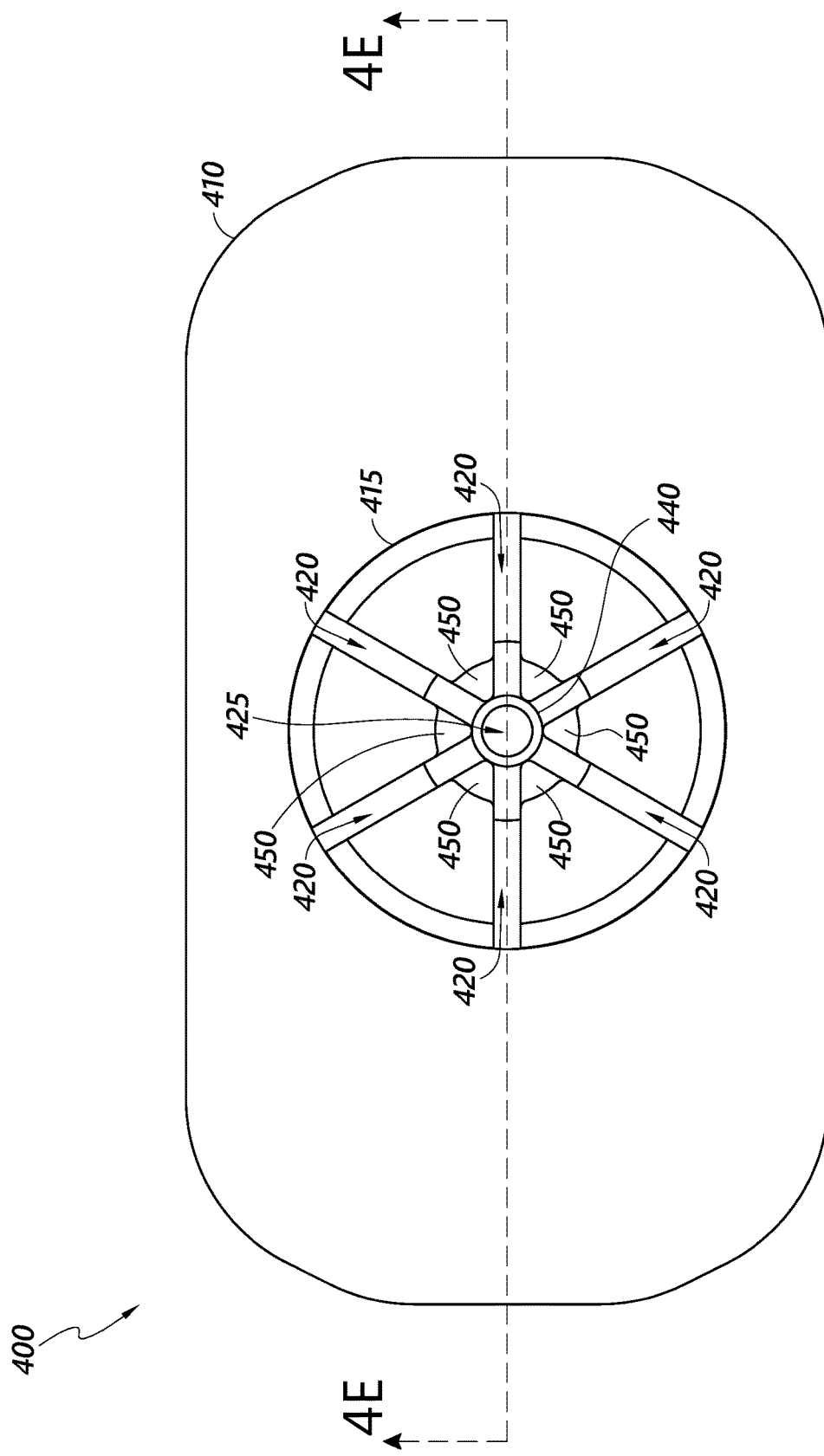

FIG. 4B depicts a bottom view of the nozzle 400, illustrating the bottom of the grip 410 and the bottom of the plunger 415. The plunger 415 has an exterior cylindrical surface 470, an interior cylindrical surface 465, and at least one surface joining the exterior cylindrical surface and the interior cylindrical surface. The at least one surface joining the exterior cylindrical surface and the interior cylindrical surface can be planar. The plunger 415 has a number of radially extending channels 420, formed as grooves, extending from the outer circumference of the plunger 415 inward toward an aperture 440. The aperture 440 is an opening into a central channel 425 that extends through the shaft 405. The channels 420 can advantageously maintain a fluid path between a swab material as it is being compressed by the plunger 415 and the central channel 425, while simultaneously direct fluid expressed from the outer surface of the swab material toward the central channel 425. Beneficially, this can increase the amount of collected antibodies that are transferred through the nozzle 400 to a test device, as the swab material is likely to accumulate antibodies on its outer surface during sampling. Although six channels 420 are illustrated, greater or fewer channels can be used in other embodiments. The channels 420 can be equally spaced around the circumference of the plunger 415 or can have varied spacing. Further details of the channels 420 are discussed below.

Figure 4C:
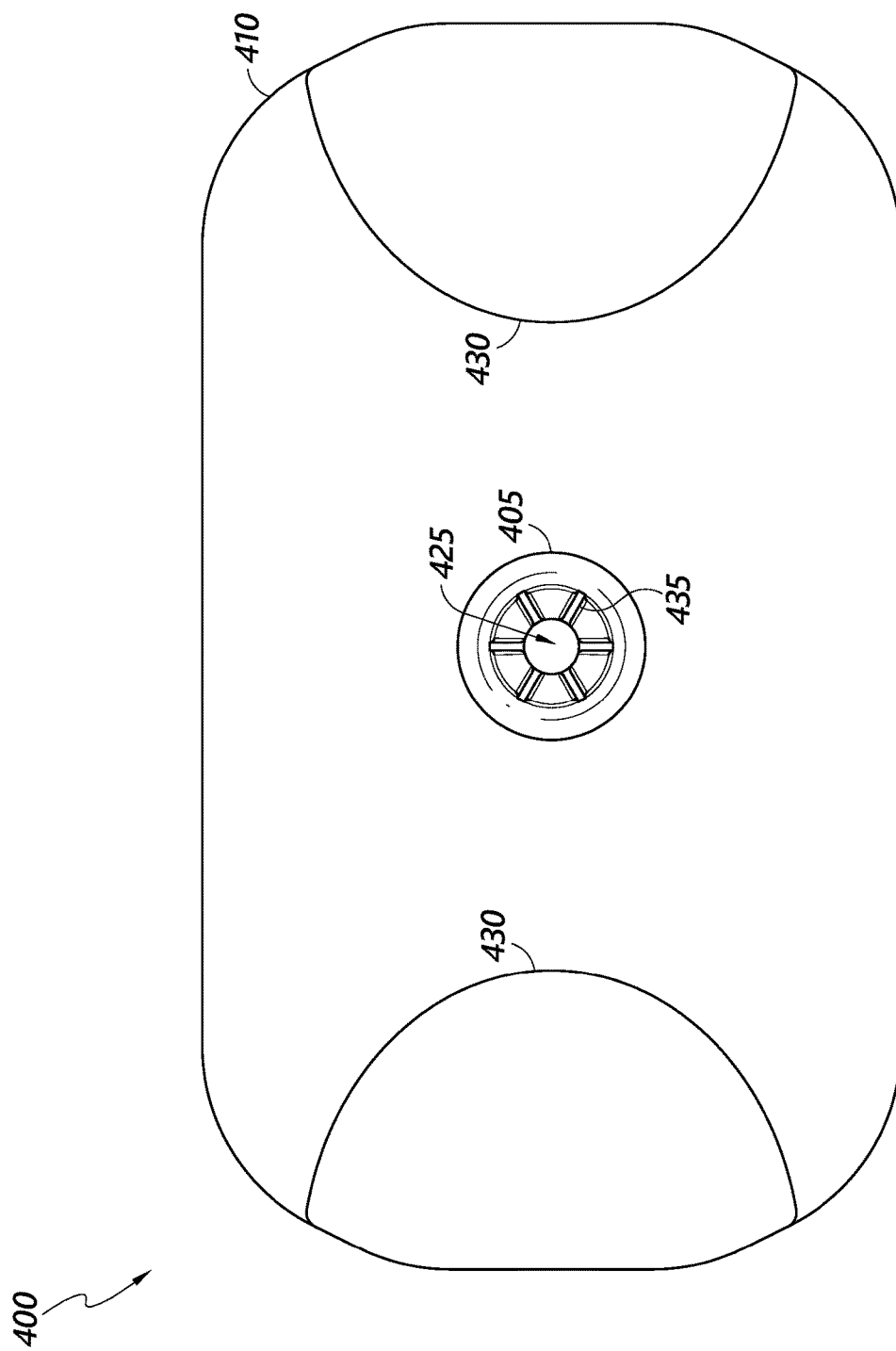

FIG. 4C depicts a top view of the nozzle 400, illustrating the top of the grip 410 and the top of the shaft 405. As depicted, the grip 410 can include raised portions 430 at opposing ends to facilitate grip by the user while engaging the nozzle 400 with a container and while moving the nozzle 400 inside the container. The shaft 405 has an aperture 435 at the end of the central channel 425 for dispensing fluid. The fluid may be, for example, dispensed onto a test device, such as shown in step 125 of FIG. 1.

The illustrated aperture 435 has a wider diameter than the central channel 425, with a tapered or curved surface having a number of grooves connecting the aperture 435 to the central channel 425. This larger diameter provides for better (for example, larger and more uniform) drop dispensing from the nozzle 400. For example, this larger diameter at the tip of the channel 425 leading to the aperture 435 helps to define the volume of liquid that a single drop will contain. The grooves (or ridges) along this surface increase the interfacial contact area, providing some additional capillary force to keep a drop from falling out of the nozzle 400 prematurely (e.g., before gathering liquid to the desired drop volume). If the channel had a straight bore tube, a drop would form during dispensing by wetting the outside of the tube prior to detaching. The resulting drop volume would be much harder to control for consistent drop dispensing than the drop volume achieved by the disclosed design, as such a design would lack capillary forces to define the drop size. Thus, the disclosed aperture 435, together with the curved or tapered surface of channel 425 leading to the aperture 435 and the grooves or ridges formed therein, are configured to provide an output liquid drip at a consistent, predetermined volume. In some embodiments, this volume can be approximately 50 µL. Other suitable volumes can also be achieved using embodiments described herein.

Figure 4D:
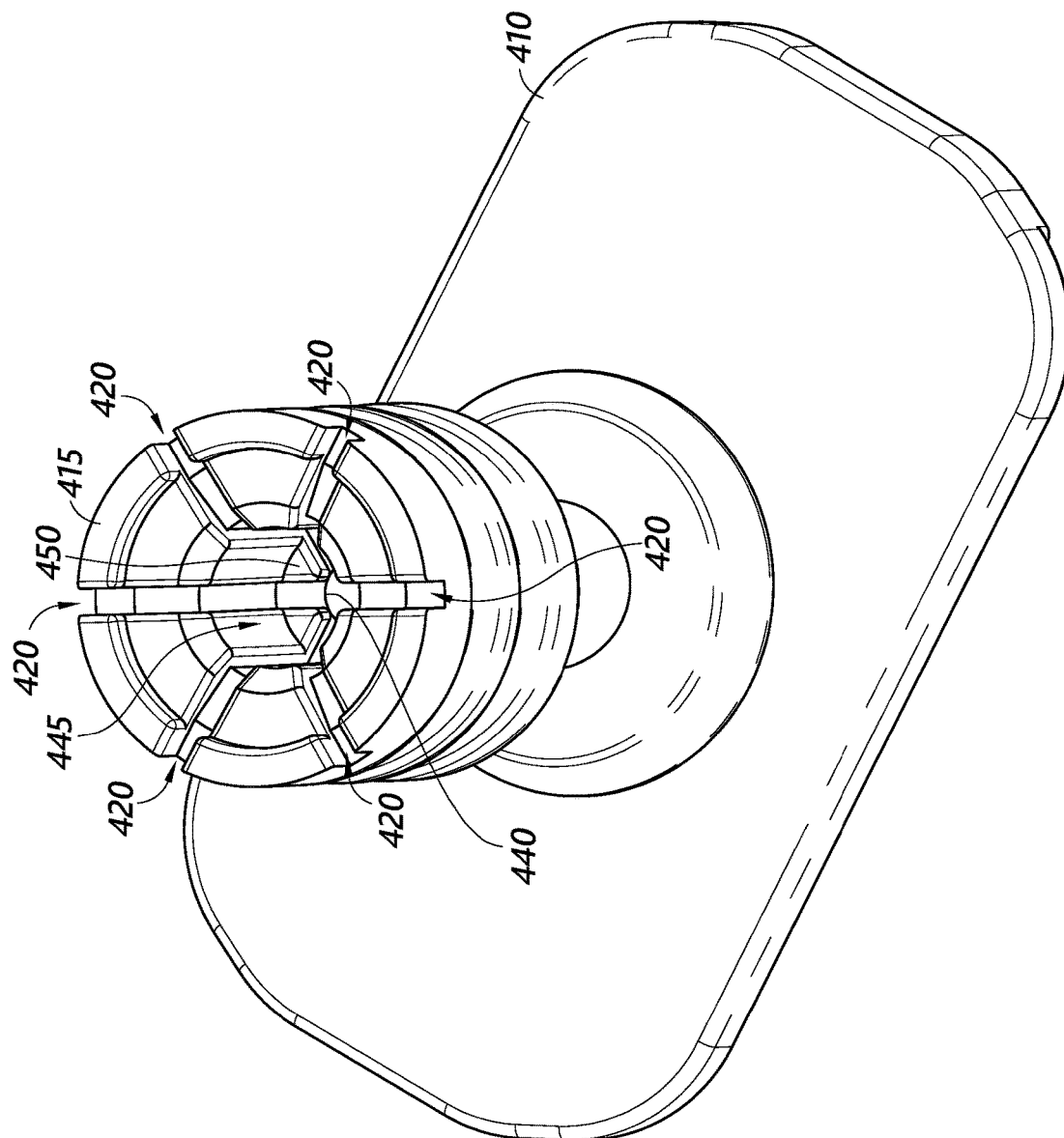

FIG. 4D depicts a bottom perspective view of the nozzle 400, illustrating the bottom of the grip 410 and the bottom of the plunger 415. As seen in the view of FIG. 4D, the nozzle 400 includes a well 445 formed in the plunger 415 as well as a number of protrusions 450 extending beyond the aperture 440 into the well 445. The protrusions 450 can be formed as raised sections of the plunger 415 between the channels 420. In use, the well 445 can receive an intermediate portion 340 of the handle 310 after the handle 310 is broken at the break point 330 within container 200. The broken end of the intermediate portion 340 and any remaining burr of the break point 330 can engage the triangular (or substantially triangular, as one side may be curved due to the cylindrical wall of the well 445) surfaces of the protrusions 450 as the nozzle 400 compresses the swab material 350. This can prevent the intermediate portion 340 and any remaining burr of the break point 330 from occluding the aperture 440, which would have the potential to block fluid flow out of the nozzle 400.

Figure 4E:
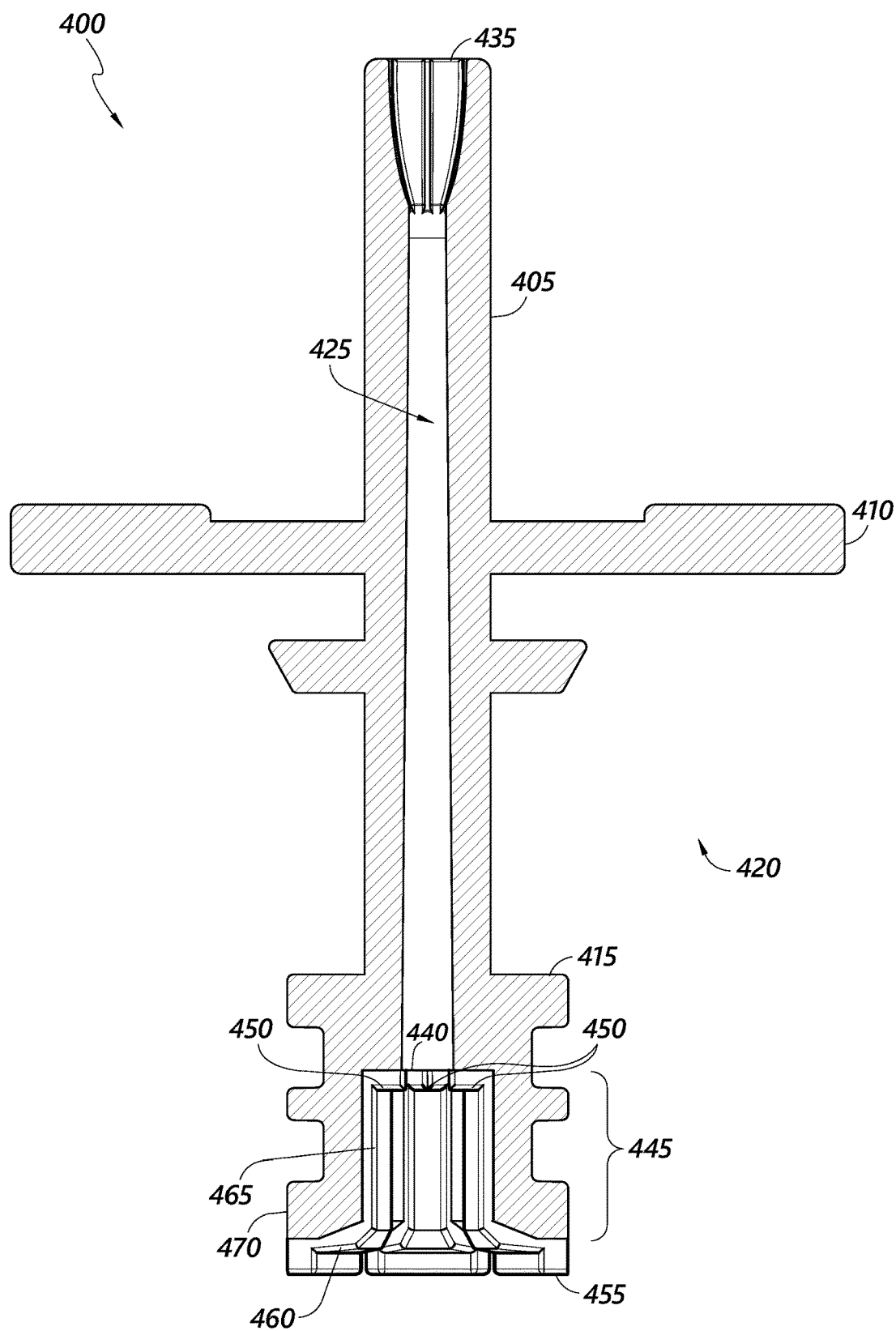
Figure 4F:
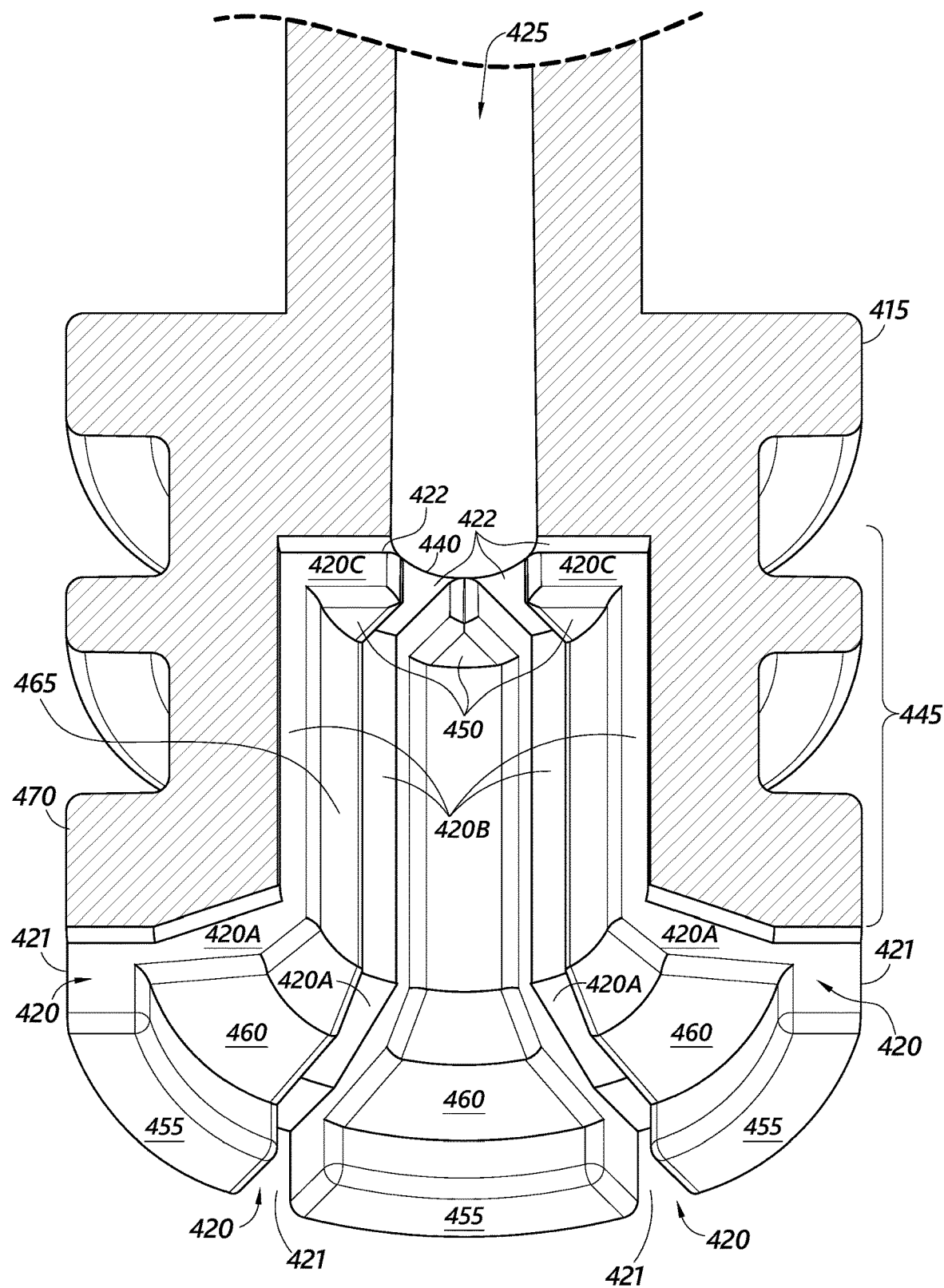

FIG. 4E depicts a cross-sectional view of the nozzle 400. The view of FIG. 4E depicts the central channel 425 extending through the entire shaft 405 as well as the interior wall 465 of the well 445 in the plunger 415. FIG. 4F depicts a portion of the cross-sectional view of FIG. 4E with a backwards tilt to illustrate the channels 420 and protrusions 450 more clearly. The view of FIG. 4F also illustrates the stepped configuration of the plunger 415. FIGS. 4E and 4F are discussed together below.

The stepped configuration of the plunger 415 includes rim 455, intermediate surface 460, protrusions 450, and aperture 440. Plunger 415 has a lowest surface formed as a rim 455 extending around the perimeter of the plunger 415, where "lowest" and "below" as used here indicates closest/closer to a swab material and the bottom of tube 215 in use with the nozzle 400 positioned partly within the tube 215. The rim 455 can operate to fully compress the outer surface of the absorbent swab material 350 against the lower surface 230 of the interior 225 of the container 215. When the swab material 350 is being compressed by the plunger 415, the rim 455 may be in direct physical contact with a border portion 351C of swab material 350 that is not directly below the flange 345 (see, for example, FIG. 3C). This direct physical contact between the rim 455 and the portion 351C of swab material 350 may facilitate very tight compression of the swab material 350 with relatively little force being applied by the user along the longitudinal axis of the nozzle 400. Inwardly from this rim is an intermediate surface 460 positioned closer to the aperture 440 than the rim 455 along the longitudinal axis of the nozzle 400. The intermediate surface 460, in use, compresses a central portion of the swab material against the lower surface 230. The interior surface 460 may be in direct physical contact with the flange 345 of the swab 300 during compression. The intermediate surface 460 can taper to the interior wall 465 of the well 445. The well 445 leads to the protrusions 450 which extend below the aperture 440.

Each channel 420 can have an entrance aperture 421 located along the outer circumference of the plunger 415. The height of the aperture 421 along the longitudinal axis (extending through the center of the central channel 425) can be the greatest height of a channel 420, for example to prevent occlusion with compressed swab material and maintain an open fluid path during compression. The entrance aperture 421 can lead to a first segment 420A formed as a groove along a portion of the intermediate surface 460. The first segment 420A can lead to a second segment 420B formed as a groove along a portion of the interior wall 465 of the well 445, with the second segment 420B running parallel to the longitudinal axis. The first segment 420A can taper toward the second segment 420B as illustrated. The second segment 420B can lead to a third segment 420C running perpendicular to the longitudinal axis. The third segment 420C, in turn, leads to an exit aperture 422 in fluid communication with the aperture 440 into the central channel 425. Thus, fluid entering the entrance aperture 421 can travel through the first segment 420A to the second segment 420B, from the second segment 420B to the third segment 420C, through the third segment 420C to exit through the exit aperture 422 into the aperture 440 leading into the central channel 425. The fluid can be drawn into the central channel 425 via gravity when the nozzle is inverted, and/or the fluid can be drawn into the central channel 425 by action of the nozzle compressing the swab material, which decreases the primary interior volume 225 and forces at least a portion of the fluid up into the central channel 425. It should be noted, however, that fluid can advantageously enter the channel 420 at any point along the first segment 420A, second segment 420B, and third segment 420C because the entire channel 420 is open to the well 445. Beneficially, the first, second, and third segments of the channel 420 maintain an open fluid path for delivering extraction fluid and sampled antibodies from the swab material 350 to the aperture 440 even in the presence of the swab material and/or intermediate portion 340 of the handle 310.

Figure 4G:
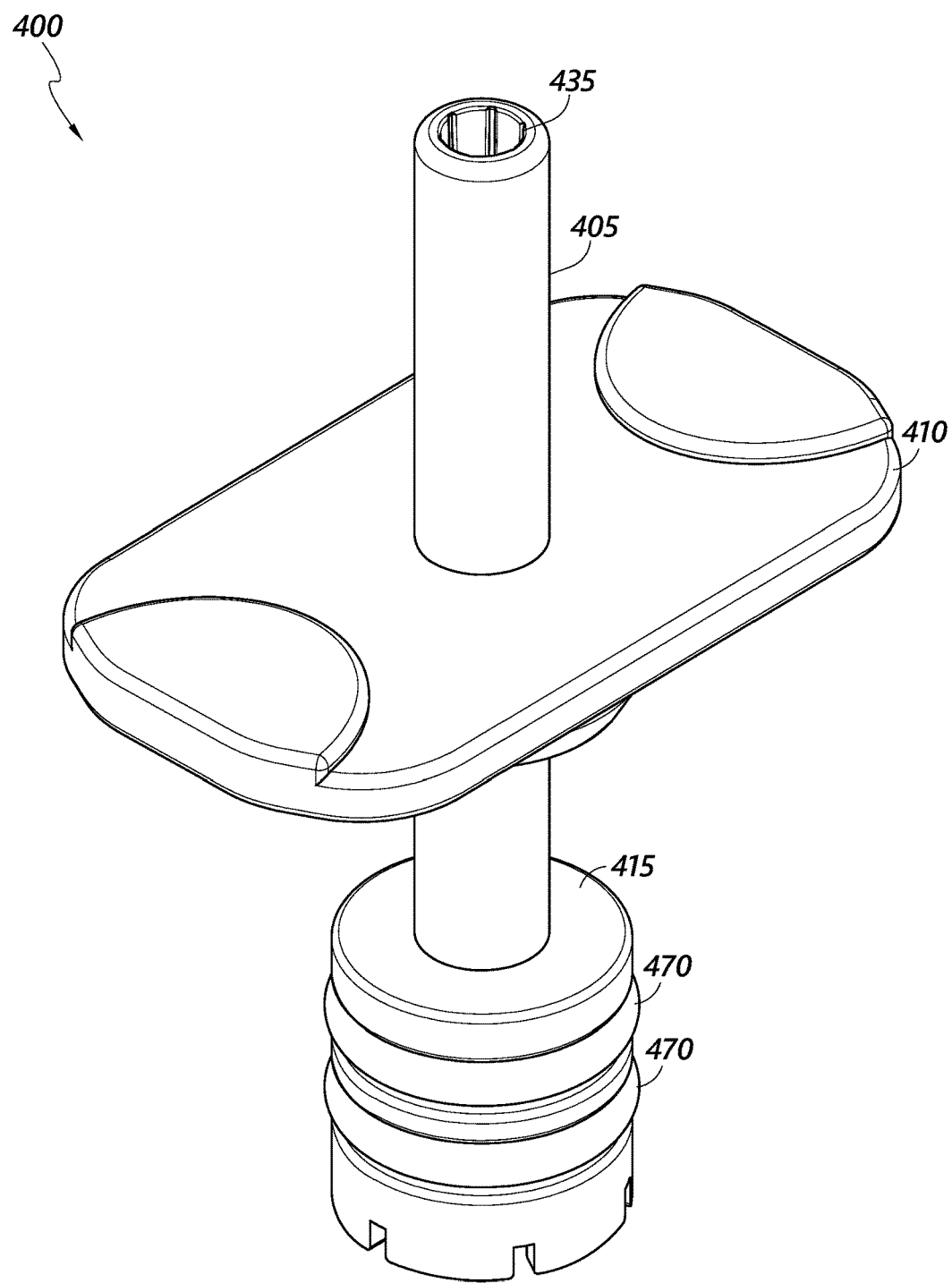

As described above, the flange 345 of the handle can be sized to rest within the inner perimeter of the rim 455 when the nozzle is pushed downward over the remaining portion of the handle within the container 200. The flange 345 provides a rigid structure by which to transfer pressure applied to the nozzle 500 to the swab material 350 in a consistently distributed manner so that the flexible swab material 350 compresses down uniformly and efficiently. At the same time, however, the flange 345 could have the potential to interfere with the flow of fluid into the channel 425. The radially extending grooves 420 allow the disclosed collection device to achieve both the desired compression and the desired fluid flow for antibody extraction by positioning the entrance apertures 421 so that they that are not blocked by the flange 345 or by compressing swab material 350. Further, this resting of the flange 345 within the inner perimeter of the rim 455 can beneficially aid in collecting fluid expressed from the outer surface 351B, as the fluid path to the nozzle channel 425 begins at apertures 421 of the grooves 420 and a direct, central path to the channel 425 is at least partially blocked by the flange 345 in the disclosed example. [0085] FIG. 4G depicts a perspective view of the nozzle 400, illustrating the shaft 405, the aperture 435, the grip 410, and the plunger 415 with elastomeric sealing elements 470 placed in the recesses 425 of the plunger 415. In the disclosed example, the elastomeric sealing elements 470 include two o-rings spaced apart along the longitudinal axis of the nozzle 400, but a fluid-tight seal may also be achieved with one o-ring. Other sealing mechanisms and configurations are suitable. For example, in other embodiments the recesses can be omitted and an elastomeric sleeve can surround the outer surface of the plunger 415.

Embodiments of the present technology can include other suitable nozzles in addition to the nozzle 400 described with reference to FIGS. 4A-4G. In one non-limiting implementation, a non-compressible porous material (for example a frit) is provided at the bottom of the plunger 415 and compresses the swab material 350 when the nozzle 400 translates along the longitudinal axis of the container 200. The non-compressible porous material can achieve a function similar to that of the channels 420. For example, the non-compressible porous material can advantageously maintain a fluid path between the swab material as it is being compressed by the plunger 415 and the central channel 425, while simultaneously directing fluid expressed from the outer surface of the swab material toward the central channel 425. A hole can be provided in the center of the non-compressible porous material to accommodate the broken end 330 and intermediate portion 340 of the handle 310 within container 200. For instance, the broken end of the intermediate portion 340 can engage and be received within the center hole of the non-compressible porous material as the nozzle 400 compresses the swab material 350. In some instances, the non-compressible porous material is provided on the nozzle 400 in lieu of the well 445.

The material, porosity, and dimensions of the non-compressible porous material can be optimized to ensure a sufficient amount of extraction solution for capillary flow along an assay strip (or other test device), and a sufficient amount of analyte of interest is extracted from the swab material into the solution. For example, in some cases, the non-compressible porous material may retain some volume of extraction solution that will not flow toward the central channel 425 for application to the test device, but the materials, porosity, and/or dimensions of the non-compressible porous material can be selected to account for the volume of retained extraction solution. In one non-limiting embodiment, the non-compressible porous material is a foam, sponge, or frit part composed of pores whose cavities are connected to one another, permitting fluidic communication throughout the part. The non-compressible porous material can be provided in a variety of suitable shapes, including but not limited to cylinders and rings. Suitable materials for the non-compressible porous material include, but are not limited to, ultra-high molecular weight polyethylene (UHMWPE), high-density polyethylene (HDPE), polypropylene (PP), polytetrafluoroethylene (PTFE), polyvinylidene fluoride (PVDF), ethylene vinyl acetate (EVA), polyethersulfone (PES), polyurethane (PU), and PE/PP co-polymer. In one non-limiting example, the non-compressible porous material is a polyethersulfone (PES) frit by Porex®. The polyethersulfone frit can exhibit low protein-binding properties, thereby maximizing the amount of analyte of interest that is extracted from the swab material and travels in the extraction solution through the channel 425.

Figure 5A:
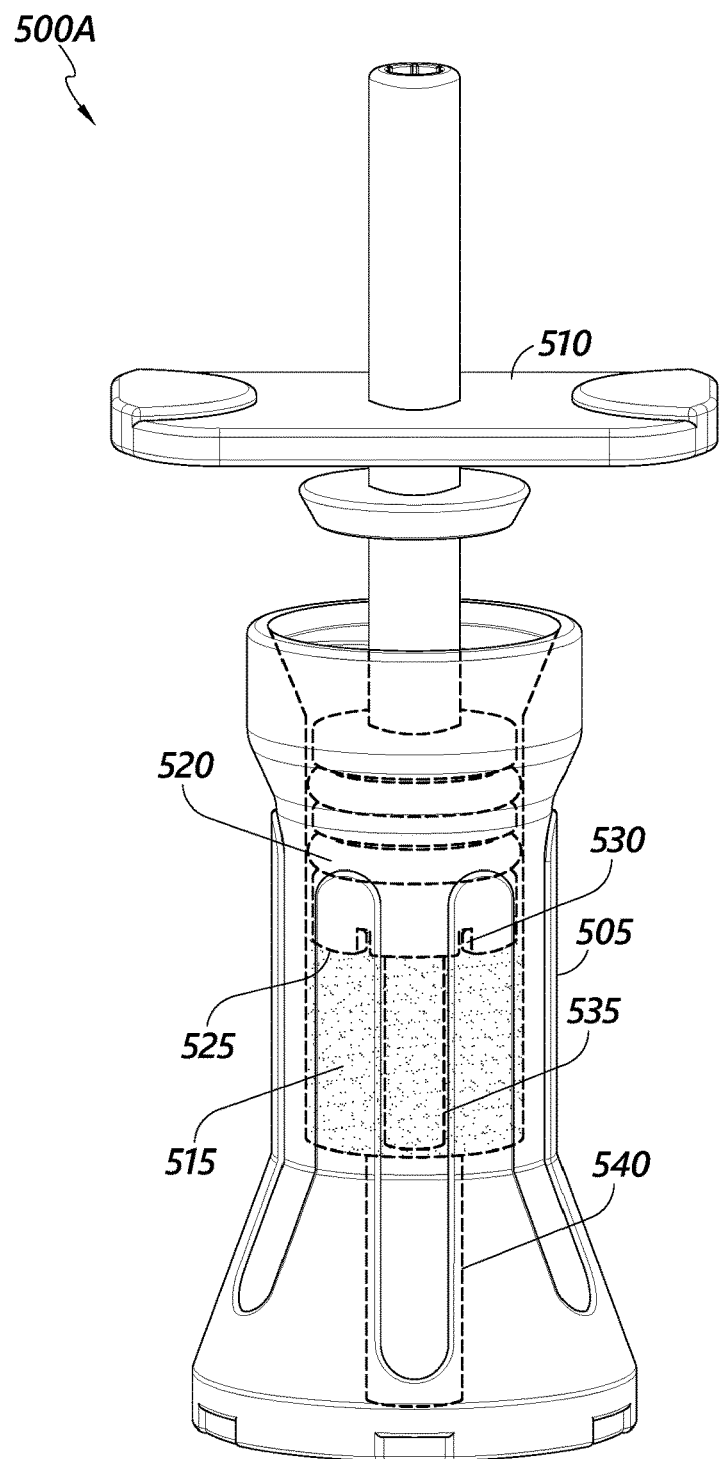
FIGS. 5A and 5B illustrate an example serological fluid collection device in various states of use.

FIG. 5A depicts a photograph of an example serological fluid collection device in a first state 500A of use. In this state 500A, the nozzle 510 (e.g., nozzle 400) is inserted into the tube 505 (e.g., tube 215) with the elastomeric seal 520 (e.g., sealing element 470) engaging an inner surface of the main body of the tube 505. The lower surface 525 of the nozzle 510 is positioned in contact with an uncompressed swab material 515 (for example, the swab material 350 with the handle 310 broken) with the channels 530 positioned above the material. As seen in FIG. 5A, the rim of the nozzle 510 (e.g., rim 455) is in direct physical contact with a portion (e.g., portion 351C) of the swab material 350. Because the elastomeric seal 520 engages an inner surface of the main body of the tube 505 to create a fluid-tight interface between these components, the central channel of the nozzle is the only fluid path out of the chamber created within the tube 505 below this seal. Though not visible in this photograph, a dashed line 535 indicates the position of a distal portion of the handle (e.g., distal portion 355) embedded within the swab material 515. The dashed line 540 indicates the position of a well in the tube 505 that can receive this distal portion 535. As illustrated in FIG. 5A, the distal portion 535 is not yet within the well 540 (e.g., well 235).

Figure 5B:
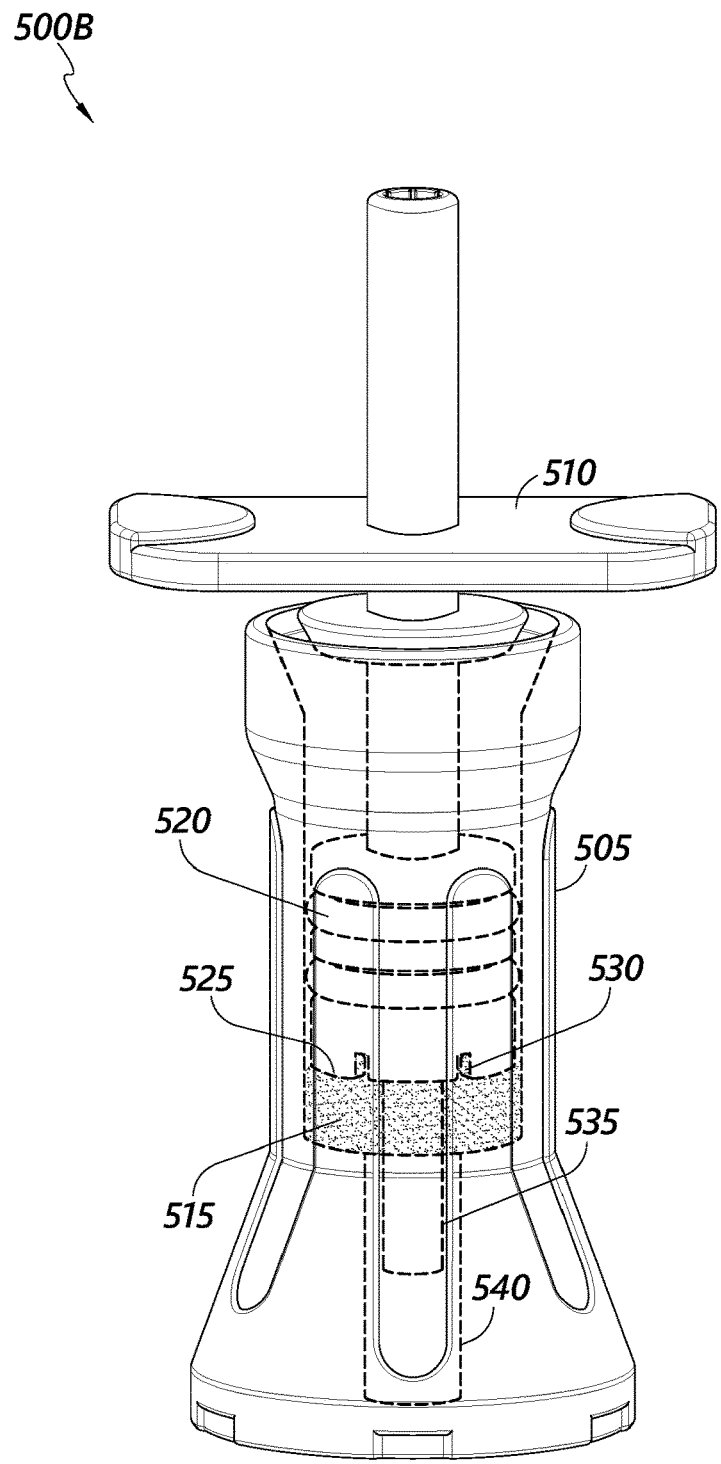

FIG. 5B depicts a photograph of the example serological fluid collection device in a second state 500B of use. Between the first state 500A of use and the second state 500B of use, the nozzle 510 has translated in a downward direction along the longitudinal axis of the tube 505 and compressed the swab material 350 at the bottom of the tube 505. Between states 500A and 500B, or at state 500B, a user can invert the device over a testing device to deliver the fluid sealed within the container to the testing device. In the second state 500B, the swab material 515 is fully compressed by the lower surface 525 of the nozzle 510. As illustrated, the channels 530 remain open to maintain a fluid path to the central channel of the nozzle 510. Though not visible in this photograph, the dashed line 535 indicates how the position of the distal portion of the handle embedded within the swab material 515 now extends into the well 540 of the tube 505, for example as shown in step 125 of FIG. 1. This allows the swab material to be compressed to a maximum extent to expel absorbed extraction fluid, thereby flushing collected antibodies out through the nozzle 510 to the testing device.

Figure 6:
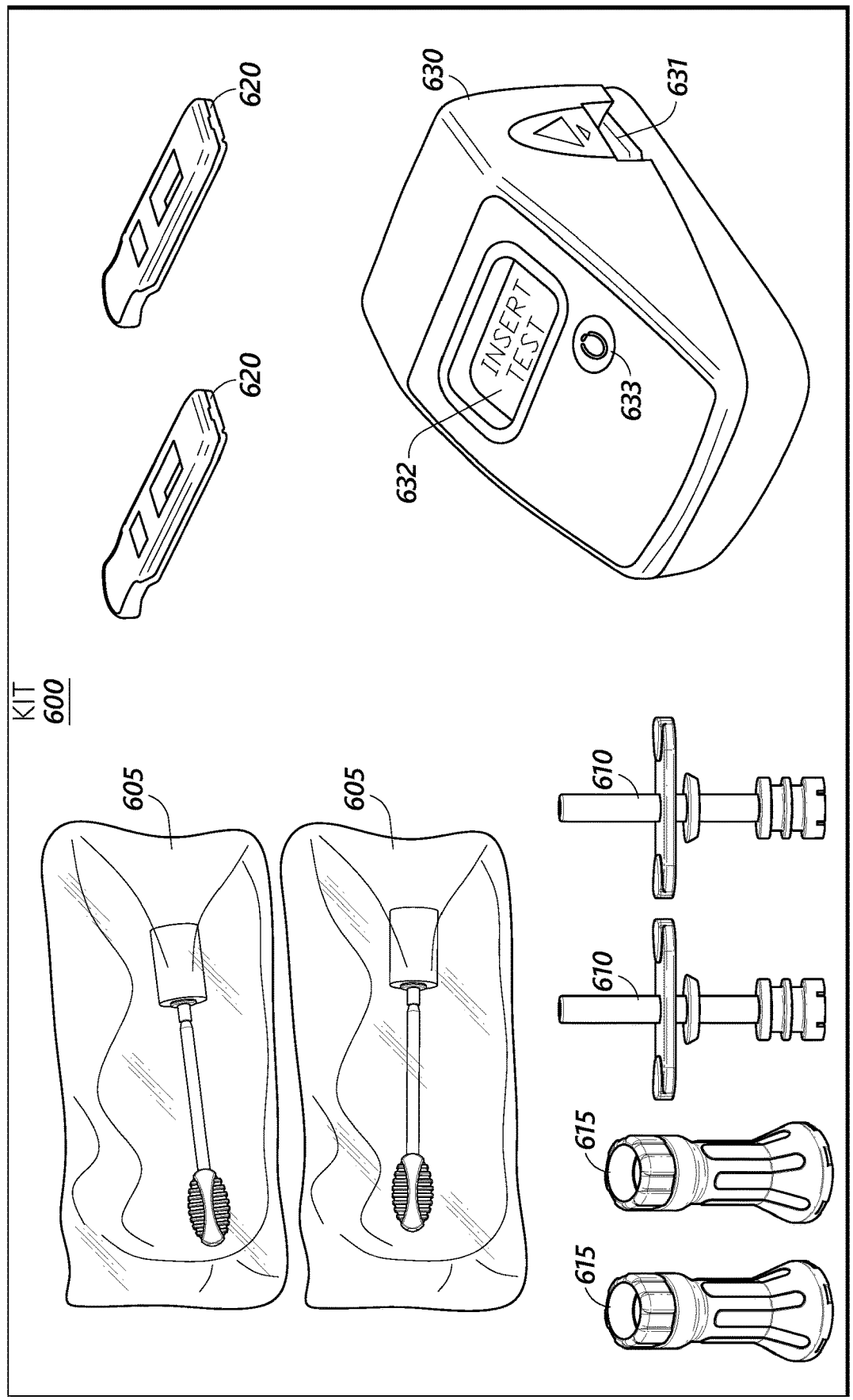
FIG. 6 illustrates an example kit for collection and analysis of serological fluid.

FIG. 6 illustrates an example kit 600 for collection and analysis of serological fluid. The exact numbers of the illustrated components of the kit 600 are for purposes of example and are not intended to be limiting. The kit 600 can include one or more swabs 605, one or more containers 615, one or more nozzles 610, one or more test cartridges 620, and optionally one or more assay reader devices 630. The swab 605 can be the swabs 140, 300 described above. The container 615 can be the containers 130, 200 described above. The nozzle 610 can be the nozzles 150, 400 described above.

The test cartridge 620 can be the test cartridge 160 described above, for example including an assay test strip configured to undergo a change in an optically-detectable characteristic upon contact between a test region and any of the antibodies described herein. The assay test strips are housed in a test cartridge 620 designed to interface with the testing device 630, a compact, portable, robust optoelectronic instrument described in more detail below. The assays can use development of a colorimetric signal using any suitable mechanism to identify the presence of any given analyte of interest. In one non-limiting example, the assays use development of a colorimetric signal via deposition of an enhanced colloidal-gold particle at the test line(s) to identify the presence of a given analyte of interest. The assay test strips can be designed with spatially-distinct zones including positive and negative control features, and separate test line positions for a plurality of different analytes, for example 3 or 4 different analytes. The assay run time can be 10 minutes, after which the test cartridge 620 is inserted into the testing device 630 for test analysis and results interpretation. Dwell time in the testing device 630 can be approximately 10 seconds. The display 632 of the testing device 630 can then display the assay results to the operator. The testing device 630 can read cartridges 620 adapted with antigens to be able to detect whether protective levels of antibodies are present. The testing device 630 can distinguish between various assays using any suitable mechanism, for example by reading a printed barcode on the top face of the cartridge 620.

The testing device 630 can be an assay reader device having an aperture 631 for receiving an assay test strip and cartridge 620 and positioning the test strip so that analyte binding regions are positioned in the optical path of imaging components located inside of the device 630. The device can also use these or additional imaging components to image a bar code on the cartridge, for example to identify which imaging techniques and analysis to perform.

Some embodiments of the device 630 can be configured to perform an initial scan, for example using a bar code scanner to image one or more bar codes. A bar code can identify the type of test to be performed, the person conducting the test, the location of the test, and/or the location in the facility of the test surface (for example pharmacy, nursing area, cabinet #, bed #, chair #, pump #, etc.) After reading the bar code identifier the cartridge is then inserted into the reader.

The device 630 can have a button 633 that readies the device for use and provides an input mechanism for a user to operate the device. The device 630 can also include a display 632 for displaying instructions and/or test results to the user. After insertion of the test strip, the device 630 can read a bar code on the assay test strip to identify the name and/or concentration range of the antibody or antibodies of interest. The device 630 can image the inserted test strip, and analyze the signals representing the imaged test strip to calculate results, display the results to the user, and optionally transmit and/or locally store the results. The results can be calculated and displayed as contamination with an indication of positive or negative (for example, +/−; yes/no; etc.), and/or the actual antibody concentration per volume.

Some embodiments of the device 630 may simply display the result(s) to the user. Some embodiments of the device 630 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system. The device 630 can also be programmed to automatically alert any additional personnel as required, without further input or instruction by the user, for example if test results (individual or aggregate) indicate outbreak of an infectious disease. One example of the device 630 can be fitted with a cell phone chip so that (if there is cell phone reception), test results and/or notifications can be automatically transmitted in real time to a Central Reference Laboratory, EPI headquarters, World Health Organization (WHO) offices, UNICEF offices, etc.

In some embodiments, device 630 can be a special-purpose assay reader device configured with computer-executable instructions for identifying trace concentrations of antibodies in the oral fluid samples applied to test strips. Further components of the device 630 are discussed below with respect to the diagram of FIG. 7.

In some embodiments of the kit 600, the same number of the swabs 605, containers 615, nozzles 610, and test cartridges 620 can be provided in the kit, because a single serological test involves one of each of these components. In some embodiments, two swabs 605 are provided for every one container 615, nozzle 60, and test cartridge 620 so that a second sample can be taken with a second swab 605 if the subject under test is uncooperative, a first swab 605 accidentally breaks prior to sample acquisition, or an adequate sample is not obtained with the first swab 605. The testing device 630 can be included in an initial kit or in a predetermined number of kits provided to a particular location, and an example assay reader device can be used thousands of times before requiring replacement, for example 3,000 or more.

Overview of Example Assay Reader Devices and Operations

Figure 7:
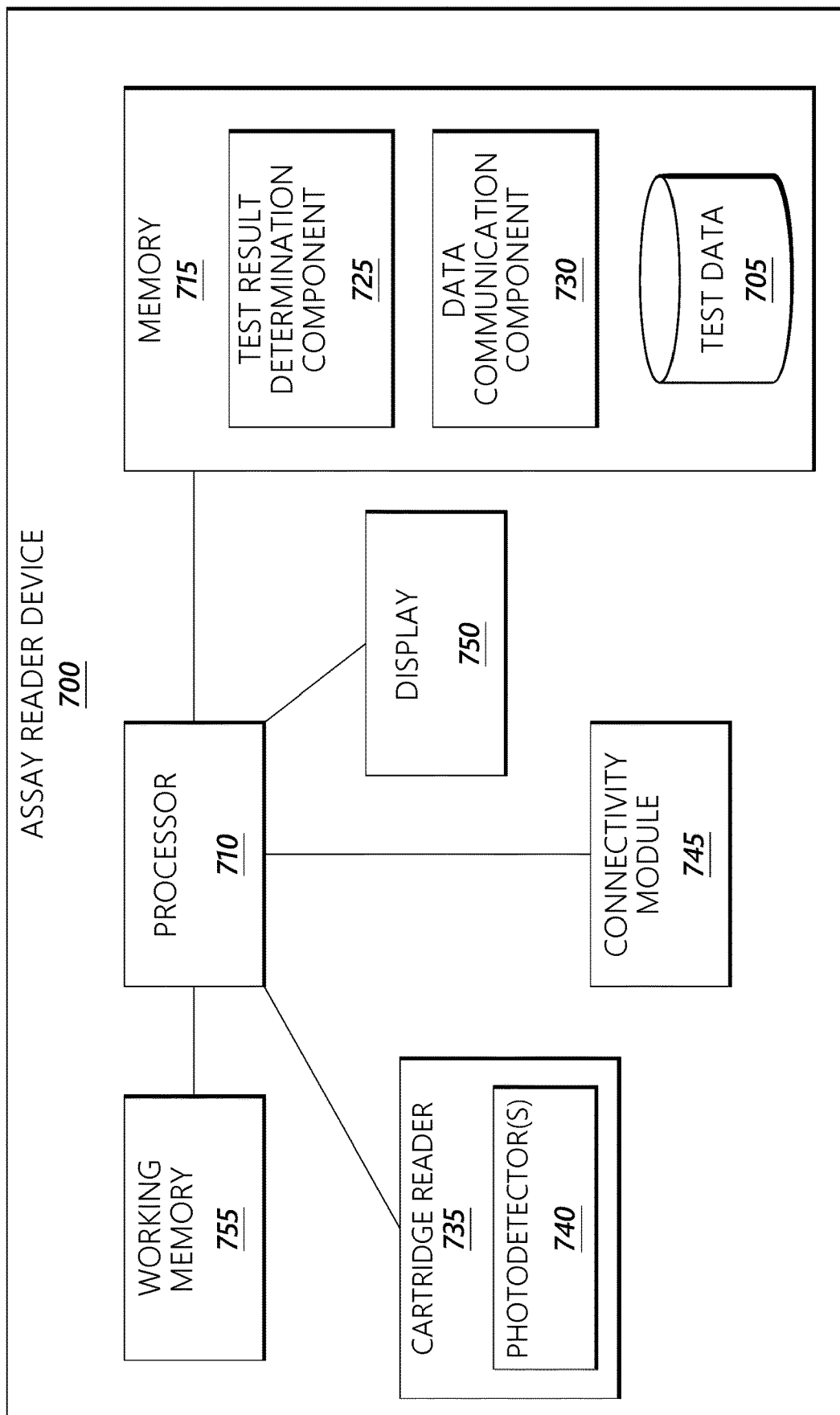
FIG. 7 depicts a high level schematic block diagram of an example testing device.

FIG. 7 illustrates a schematic block diagram of one possible embodiment of components of an example assay reader device 700. The components can include a processor 710 linked to and in electronic communication with a memory 715, working memory 755, cartridge reader 735, connectivity module interface 745, and display 750.

Connectivity module 745 can include electronic components for wired and/or wireless communications with other devices. For example, connectivity module 745 can include a wireless connection such as a cellular modem, satellite connection, or Wi-Fi, or via a wired connection. Thus, with connectivity module 745 the assay reader device can be capable of sending or uploading data to a remote repository via a network and/or receiving data from the remote repository. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other testing devices to enable electronic test result transmission, storage, analysis and/or dissemination without requiring separate intervention or action by the user of the device. In some embodiments connectivity module 745 can provide connection to a cloud database, for example a server-based data store. The cloud based connectivity module can enable ubiquitous connectivity of assay reader devices without the need for a localized network infrastructure.

The cartridge reader 735 can include one or more photodetectors 740 for reading an assay held in an inserted cartridge and optionally any information on the inserted cartridge, for example a barcode printed on the cartridge. The cartridge reader 735 can send image data from the one or more photodetectors to the processor 710 for analysis of the image data representing the imaged assay to determine a test result of the assay. The cartridge reader 735 can further send image data from the one or more photodetectors representing the imaged cartridge for use in determining which one of a number of automated operating processes to implement for imaging the assay and/or analyzing the image data of the assay. The photodetector(s) 740 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 735 can also include a component for detecting cartridge insertion, for example a mechanical button, electromagnetic sensor, or other cartridge sensing device. An indication from this component can instruct the processor 710 to begin an automated assay reading process without any further input or instructions from the user of the device 700.

Processor 710 can be configured to perform various processing operations on image data received from the cartridge reader 735 and/or connectivity module interface 745 in order to determine and store test result data, as will be described in more detail below. Processor 710 may be a general purpose processing unit implementing assay analysis functions or a processor specially designed for assay imaging and analysis applications. The processor 710 can be a microcontroller, a microprocessor, or ASIC, to name a few examples, and may comprise a plurality of processors in some embodiments.

As shown, the processor 710 is connected to a memory 715 and a working memory 755. In the illustrated embodiment, the memory 715 stores test result determination component 725, data communication component 730, and test data repository 705. These modules include instructions that configure the processor 710 of device 700 to perform various module interfacing, image processing, and device management tasks. Working memory 755 may be used by processor 710 to store a working set of processor instructions contained in the modules of memory 715. Alternatively, working memory 755 may also be used by processor 710 to store dynamic data created during the operation of device 700.

As mentioned above, the processor 710 may be configured by several modules stored in the memory 715. The test result determination component 725 can include instructions that call subroutines to configure the processor 710 to analyze assay image data received from the photodetector(s) 740 to determine a result of the assay. For example, the processor can compare image data to a number of templates or pre-identified patterns to determine the test result. In some implementations, test result determination component 725 can configure the processor 710 to implement adaptive read processes on image data from the photodetector(s) 740 to improve specificity of test results and to reduce false-positive results by compensating for background and non-specific binding.

The data communication component 730 can determine whether a network connection is available and can manage transmission of test result data to determined personnel and/or remote databases. If the device 700 is not presently part of a network, the data communication component 730 can cause local storage of test results and associated information in the test data repository 705. In some case, the device 700 can be instructed to or automatically transmit the stored test results upon connection to a network. If a local wired or wireless connection is established between the device 700 and another computing device, for example a hospital, clinician, or patient computer, the data communication component 730 can prompt a user of the device 700 to provide a password in order to access the data in the repository 705.

The processor 710 can be configured to control the display 750 to display captured image data, imaged barcodes, test results, and user instructions, for example. The display 750 may include a panel display, for example, a LCD screen, LED screen, or other display technologies, and may implement touch sensitive technologies.

Processor 710 may write data to data repository 705, for example data representing captured images of assays, instructions or information associated with imaged assays, and determined test results. While data repository 705 is represented graphically as a traditional disk device, those with skill in the art would understand that the data repository 705 may be configured as any storage media device. For example, data repository 705 may include a disk drive, such as a hard disk drive, optical disk drive or magneto-optical disk drive, or a solid state memory such as a FLASH memory, RAM, ROM, and/or EEPROM. The data repository 705 can also include multiple memory units, and any one of the memory units may be configured to be within the assay reader device 700, or may be external to the device 700. For example, the data repository 705 may include a ROM memory containing system program instructions stored within the assay reader device 700. The data repository 705 may also include memory cards or high speed memories configured to store captured images which may be removable from the device 700.

Although FIG. 7 depicts a device having separate components to include a processor, cartridge reader, connectivity module, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 7 illustrates a number of memory components, including memory 715 comprising several modules and a separate memory 755 comprising a working memory, one of skill in the art would recognize several embodiments utilizing different memory architectures. For example, a design may utilize ROM or static RAM memory for the storage of processor instructions implementing the modules contained in memory 715. The processor instructions may be loaded into RAM to facilitate execution by the processor 710. For example, working memory 755 may comprise RAM memory, with instructions loaded into working memory 755 before execution by the processor 710.

The device 700 can further include other components not illustrated, for example one or more input devices, one or more connection/data transfer ports, one or more additional output devices such as an audio output device, and a power source/interface. The device may additionally include a transmitter and a receiver, for example as part of the connectivity module 745. The transmitter and receiver may be jointly referred to as a transceiver. The transceiver may be coupled to one or more antennas for transmitting and/or receiving wireless signals.

Implementing Systems and Terminology

Implementations disclosed herein provide systems, methods and apparatus for detection of the presence and/or quantity of antibodies. One skilled in the art will recognize that these embodiments may be implemented in hardware or a combination of hardware and software and/or firmware.

The assay reading functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. Thus, the present invention is not intended to be limited to the implementations shown herein but is to be accorded the widest scope consistent with the principles and novel features disclosed herein.

What is claimed is:

1. A collection device comprising:
   a tubular body having an interior volume comprising a primary interior volume having a lower surface and a well extending from the lower surface;
   a material configured to collect oral fluid containing antibodies from gums of a patient;
   a handle having a distal end coupled to the material, a proximal end spaced apart from the distal end, an elongate length extending therebetween, and a break point along the elongate length;
   an extraction solution in the tubular body, the extraction solution formulated to remove collected antibodies from the material; and
   a nozzle comprising:
      a shaft,
      a channel extending through the shaft,
      a plunger at one end of the shaft, the plunger having an exterior cylindrical surface, an interior cylindrical surface, and at least one surface joining the exterior cylindrical surface and the interior cylindrical surface, and
      a plurality of radially extending channels each forming a fluid path leading from the exterior cylindrical surface to the channel extending through the shaft.

2. The collection device of claim 1, wherein the plunger further comprises:
   a rim along the exterior cylindrical surface forming a lowest surface of the at least one surface; and
   a plurality of protrusions around an aperture into the channel, the plurality of protrusions formed between portions of the plurality of radially extending channels.

3. The collection device of claim 2, wherein each of the plurality of channels comprises a first segment formed as a groove in at least the rim, a second segment formed as a groove in a portion of the interior cylindrical surface of the plunger, and a third segment formed between two adjacent protrusions of the plurality of protrusions, wherein the first, second, and third segments form the fluid path leading from the exterior cylindrical surface to the channel extending through the shaft.

4. The collection device of claim 1, wherein the break point of the handle is positioned along the elongate length such that the distal end of the handle, the material, and an intermediate portion extending along the elongate length between the material and the break point fit entirely within the interior volume of the tubular body.

5. The collection device of claim 4, wherein the collection device is configured such that, in use, with the at least one surface of the plunger compressing the material against the lower surface of the interior volume, the distal end of the handle extends into the well.

6. The collection device of claim 1, wherein the material comprises an open-cell ester foam.

7. The collection device of claim 1, wherein the nozzle further comprises a seal around the exterior surface of the plunger and configured to substantially seal the interior volume of the tubular body with the plunger inserted into the tubular body and the material positioned between the lower surface and the plunger.

8. A fluid collection device comprising:
   a tubular body having an interior volume comprising a primary interior volume having a lower surface and a well extending from the lower surface,
   a material configured to collect fluid,
   a breakable handle having a distal end coupled to the material, a proximal end spaced apart from the distal end, an elongate length extending therebetween, and a break location along the elongate length,
   a solution in the tubular body, the solution formulated to remove particles in the collected fluid from the material, and
   a nozzle comprising:
      a shaft,
      a channel extending through the shaft,
      a plunger at one end of the shaft, the plunger having a plurality of channels formed in at least a bottom surface of the plunger, each of the plurality of channels forming a fluid path leading from an exterior cylindrical surface of the plunger to the channel extending through the shaft.

9. The fluid collection device of claim 8, wherein the plunger further comprises:
   a rim along the exterior cylindrical surface forming a lowest surface of the bottom surface; and
   a plurality of protrusions around an aperture into the channel, the plurality of protrusions formed between portions of the plurality of channels.

10. The fluid collection device of claim 9, wherein each of the plurality of channels comprises a first segment formed as a groove in at least the rim, a second segment formed as a groove in a portion of an interior cylindrical surface of the plunger, and a third segment formed between two adjacent protrusions of the plurality of protrusions, wherein the first, second, and third segments form the fluid path leading from the exterior cylindrical surface to the channel extending through the shaft.

11. The fluid collection device of claim 8, wherein the break location of the handle is positioned along the elongate length such that the distal end of the handle, the material, and an intermediate portion extending along the elongate length between the material and the break location fit entirely within the interior volume of the tubular body.

12. The fluid collection device of claim 8, wherein the device is configured such that, in use, with the bottom surface of the plunger compressing the material against the lower surface of the interior volume, the portion of the handle distal to the break location partially extends into the well.

13. The fluid collection device of claim 8, wherein the material comprises a foam having a porosity of about 40 PPI to about 60 PPI.

14. The fluid collection device of claim 8, wherein the nozzle further comprises a seal configured to seal the interior volume of the tubular body when the plunger is inserted into the tubular body.

15. A method of testing seroprotection using oral fluid, the method comprising:

contacting a material secured to a handle along the gums of a patient to collect oral fluid containing antibodies;

inserting a portion of the handle, the material, and any antibodies collected thereon into a tube;

breaking the handle such that a portion of the handle having the material secured thereto remains within the tube;

inserting a portion of a nozzle into the tube, the nozzle comprising:
a shaft,
a channel extending through the shaft, and
a plunger at one end of the shaft, the plunger comprising a plurality of channels formed in at least a bottom surface of the plunger, each of the plurality of channels forming a fluid path leading from an exterior cylindrical surface of the plunger to the channel extending through the shaft;

inverting the tube with the nozzle inserted partially into the tube and the material positioned within the tube;

compressing the material between an interior lower surface of the tube and the plunger;

transferring a volume of the extraction solution from the channel of the nozzle to a test device.

16. The method of claim 15, wherein the test device is an assay test strip, and wherein the method further comprises:
inserting the assay test strip into an assay reader device, and
based on an output of the assay reader device, identifying that the antibodies are present in the oral fluid.

17. The method of claim 15, wherein the tube comprises:
a primary interior volume defined by an inner wall and the lower interior surface;
a well extending from the lower interior surface; and
a volume of extraction solution within the well and at least a portion of the primary interior volume.

18. The method of claim 17, wherein compressing the material causes a distal portion of the handle embedded within the material to extend into the well of the tube.

19. The method of claim 17, wherein inserting the material into the tube causes the material to absorb at least some of the extraction fluid.

20. The method of claim 19, wherein compressing the material causes the material to express the absorbed extraction fluid, and wherein expressing the absorbed extraction fluid removes at least some of the antibodies collected on the material.

* * * * *